United States Patent
Henkin et al.

(10) Patent No.: US 11,261,237 B2
(45) Date of Patent: *Mar. 1, 2022

(54) MODIFIED PIGMENT EPITHELIUM-DERIVED FACTOR (PEDF) PEPTIDES AND USES THEREOF FOR TREATING NEOVASCULAR DISEASES, INFLAMMATORY DISEASES, CANCER, AND FOR CYTOPROTECTION

(71) Applicants: Northwestern University, Evanston, IL (US); Board of Regents of the University of Nebraska, Lincoln, NE (US)

(72) Inventors: Jack Henkin, Highland Park, IL (US); Olga Volpert, Wilmette, IL (US); Serguei Vinogradov, Omaha, NE (US); Ignacio Melgar-Asensio, Chicago, IL (US)

(73) Assignees: Northwestern University, Evanston, IL (US); Board of Regents of the University of Nebraska, Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/123,863

(22) Filed: Sep. 6, 2018

(65) Prior Publication Data

US 2018/0371060 A1 Dec. 27, 2018

Related U.S. Application Data

(63) Continuation of application No. 15/497,822, filed on Apr. 26, 2017, now Pat. No. 10,081,668.

(60) Provisional application No. 62/327,767, filed on Apr. 26, 2016.

(51) Int. Cl.
| | |
|---|---|
| *C07K 14/81* | (2006.01) |
| *A61K 47/69* | (2017.01) |
| *C07K 7/06* | (2006.01) |
| *C07K 19/00* | (2006.01) |
| *A61K 47/61* | (2017.01) |
| *A61K 47/54* | (2017.01) |
| *A61K 47/55* | (2017.01) |
| *A61K 47/64* | (2017.01) |
| *A61K 38/00* | (2006.01) |

(52) U.S. Cl.
CPC .......... *C07K 14/8121* (2013.01); *A61K 47/54* (2017.08); *A61K 47/542* (2017.08); *A61K 47/55* (2017.08); *A61K 47/61* (2017.08); *A61K 47/64* (2017.08); *A61K 47/6903* (2017.08); *A61K 47/6921* (2017.08); *A61K 47/6935* (2017.08); *A61K 47/6939* (2017.08); *C07K 7/06* (2013.01); *C07K 19/00* (2013.01); *A61K 38/00* (2013.01)

(58) Field of Classification Search
CPC .................. C07K 14/8121; A61K 47/6903
See application file for complete search history.

(56) References Cited

U.S. PATENT DOCUMENTS

| | | | |
|---|---|---|---|
| 6,358,920 B1 | 3/2002 | Blaschuk et al. | |
| 8,198,406 B2 | 6/2012 | Volpert et al. | |
| 8,278,284 B2 | 10/2012 | Miyazaki et al. | |
| 8,530,416 B2 | 9/2013 | Seger et al. | |
| 9,096,689 B2 | 8/2015 | Volpert et al. | |
| 10,081,668 B2 | 9/2018 | Henkin et al. | |
| 2010/0331263 A1 | 12/2010 | Volpert et al. | |
| 2011/0117120 A1 | 5/2011 | Sedegah et al. | |
| 2012/0316115 A1* | 12/2012 | Volpert ................ | C07K 14/811 514/13.3 |

FOREIGN PATENT DOCUMENTS

| | | |
|---|---|---|
| EP | 1265627 | 12/2002 |
| WO | WO 2013/184986 | 12/2013 |

OTHER PUBLICATIONS

Nuijens et al., 2012, Enzymatic C-terminal amidation of amino acids and peptides, Tetrahedron Letters, 53: 3777-3779.*
Veronese et al., 1999, Bioconjugation in pharmaceutical chemistry, II Farmaco, 54: 497-516.*
An et al., Glycopolymer modified magnetic mesoporous silica nanoparticles for MR imaging and targeted drug delivery. Colloids and Surfaces A: Physiochemic Eng. Aspects 2015;482:98-108.
Barber et al., The combination of intravenous bevacizumab and metronomic oral cyclophosphamide is an effective regimen for platinum-resistant recurrent ovarian cancer. J Gynecol Oncol. Jul. 2013;24(3):258-64.
Filleur et al., Two functional epitopes of pigment epithelial-derived factor block angiogenesis and induce differentiation in prostate cancer. Cancer Res. Jun. 15, 2005;65(12):5144-52.
Funatomi et al., Pentafluorophenylammonum triflate (PFPAT), an efficient practical, and cost-effective catalyst for esterification, thioesterificiation, transesterification, and macrolactone formation. Green Chemistry 2006;8(12):1022-7.
Hatano et al., Lanthanum(III) catalysts for highly efficient and chemoselective transesterification. Chem Commun (Camb). Mar. 11, 2013;49(20):1983-97.
Mirochnik et al., Short pigment epithelial-derived factor-derived peptide inhibits angiogenesis and tumor growth. Clin Cancer Res. Mar. 1, 2000;15(5):1655-63.
Park et al., Overexpression of pigment epithelium-derived factor inhibits retinal inflammation and neovascularization. Am J Pathol. Feb. 2011;178(2):688-98.

(Continued)

*Primary Examiner* — Amber D Steele
(74) *Attorney, Agent, or Firm* — Casimir Jones SC; David W. Staple

(57) ABSTRACT

Disclosed are modified pigment epithelium-derived factor (PEDF) peptides, particulate carrier prodrugs thereof, and pharmaceutical compositions comprising the peptides or particulate carrier prodrugs. The peptides, particulate carrier prodrugs, and pharmaceutical compositions may be used to treat diseases and disorders that are amenable to treatment with anti-angiogenic agents, anti-tumorigenic agents, anti-fibrotic agents, chemotherapy-protecting agents, and immune stimulating agents.

25 Claims, 16 Drawing Sheets

Specification includes a Sequence Listing.

(56) References Cited

OTHER PUBLICATIONS

Pollastri et al., The conversion of alcohols to halides using a filterable phosphine source. Tetrahedron Letters 2001;42(13):2459-60.

Stott et al., Modified crown ether catalylsist. 3. Structural parameters affecting phase transfer catalysis by crown ethers and a comparison of the effectiveness of crown ethers to that of other phase transfer catalysis. J Am Chem Soc 1980;102(14):4810-15.

Thermo Electron Corporation, N-Terminal Acetylation and C-Terminal Amidation of Peptides, Techinical Bulletin 2004; 2 pages.

Vigorov et al., Synthesis of Derivatives of the RGD Peptide with the Residues of Glutaric and Adipic Acids. Russian Journal of Bioorganic Chemistry 2014;40(2):142-150.

Xu et al., Nanoparticle diffusion in, and microrheology of, the bovine vitreous ex vivo. J Control Release. Apr. 10, 2013;167(1):76-84.

Zahedi et al., An injectable depot system for sustained intraperitoneal chemotherapy of ovarian cancer results in favorable drug distribution at the whole body, peritoneal and intratumoral levels. J Control Release. Mar. 28, 2012;158(3):379-85.

Zamiri et al., Pigment Epithelial Growth Factor Suprpresses Inflammation by Modulating Macrophage Activation. Invest Ophthalmol Vis Sci Sep. 2006;47(9):3912-18.

Zhang et al., Perivascular macrophage-like melanocyte responsiveness to acoustic trauma—a salient feature of strial barrier associated hearing loss. FASEB J. Sep. 2013;27(9):3730-40.

Zou et al., PD-L1 (B7-H1) and PD-1 pathway blocake for cancer therapy: Mechanisms, response biomarkers, and combinations. Sci Transl Med Mar. 2016; 8(328):1-15.

International Search Report and Written Opinion for PCT/US2017/029618 dated Aug. 14, 2017, 7 pages.

* cited by examiner

Figure 1

PEDF P18 from U.S. Patent No. 8,198,406

Ac-NFGYDLYRVRSSTSPTTTN-NH2

| Sequence | SEQ ID |
|---|---|
| Ac-GYDLYRVRS-NH2 | SEQ ID NO:1 ED50 = 60nm |
| Glt-Sar-GYDLYRVRS-NH2 | SEQ ID NO:2 ED50 = 30nm |
| amino-PEG12CO-Sar-GYDLYRVRS-NH2 | SEQ ID NO:3 ED50 = 30nm |
| Glt-Sar-GYNLYRVRS-NH2 | SEQ ID NO:4 ED50 = 15nm |
| amino-PEG8CO-Sar-YNLYRVRS-NH2 | SEQ ID NO:5 ED50 = 15nm |
| Sar-NH-PEG4CO-GYNLYRVRS-NH2 | SEQ ID NO:6 ED50 = 5nm |
| Adp-Sar-GYNLYRVRS-NH2 | SEQ ID NO:7 ED50 = 15nm |
| Glt-Sar-GYNLYRVP-NHEt | SEQ ID NO:8 ED50 = 5nm |
| Glt-Sar-YNLYRVQS-NH2 | SEQ ID NO:9 ED50 = 5nm |
| Adp-Sar-YNLYRVP-NHEt | SEQ ID NO:10 ED50 = 3nm |
| Adp-Sar-YNLYRVRS-NH2 | SEQ ID NO:11 ED50 = 3nm |
| Sub-NLYRVP-NHEt | SEQ ID NO:12 ED50 = NT |
| Sub-NLYRVRS-NH2 | SEQ ID NO:13 ED50 = NT | abbreviations
Glt = glutaric acid
Adp = adipic acid
Sub = suberic acid
PEG = polyethylene glycol
NHEt = ethylamide

Figure 6
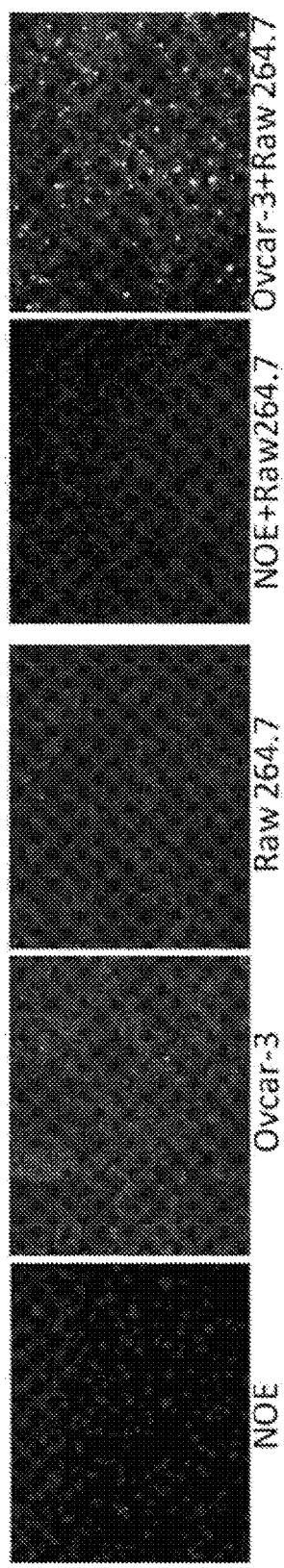
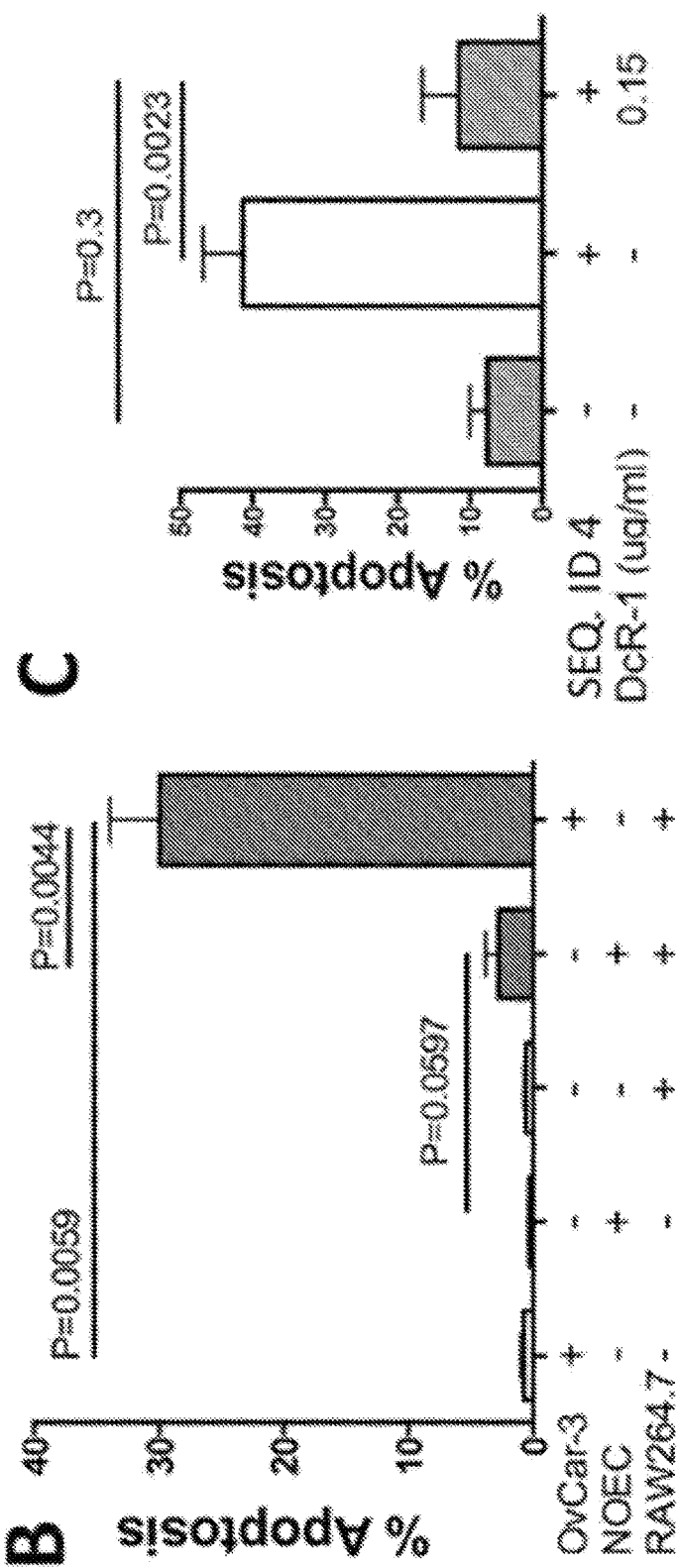

MODIFIED PIGMENT EPITHELIUM-DERIVED FACTOR (PEDF) PEPTIDES AND USES THEREOF FOR TREATING NEOVASCULAR DISEASES, INFLAMMATORY DISEASES, CANCER, AND FOR CYTOPROTECTION

CROSS-REFERENCE TO RELATED PATENT APPLICATIONS

This application is a continuation of U.S. patent application Ser. No. 15/497,822, filed Apr. 26, 2017, now U.S. Pat. No. 10,081,668, which claims the benefit of priority under 35 U.S.C. 119(e) to U.S. Provisional Application No. 62/327,767, filed on Apr. 26, 2016, each of which is incorporated herein by reference in its entirety.

STATEMENT REGARDING FEDERALLY SPONSORED RESEARCH OR DEVELOPMENT

This invention was made with government support under R24 EY022883 (University of Wisconsin Subcontract to Northwestern University, #457K273) awarded by the National Institutes of Health. The government has certain rights in the invention.

SEQUENCE LISTING

The text of the computer readable sequence listing filed herewith, titled "35570-303_SEQUENCE_LISTING_ST25", created Apr. 29, 2020, having a file size of 6,000 bytes, is hereby incorporated by reference in its entirety.

BACKGROUND

The field of the invention relates to therapeutic peptides and prodrugs thereof. In particular, the field of the invention relates to therapeutic peptides which duplicate some of the beneficial effects of pigment epithelium-derived factor (PEDF), to which they are related, including anti-angiogenic, anti-tumorigenic, and immunomodulatory properties.

Pigment epithelium-derived factor (PEDF) also known as serpin F1 (SERPINF1), is a multifunctional secreted protein that has anti-angiogenic, anti-tumorigenic, immunomodulatory and neurotrophic functions. PEDF is being researched as a therapeutic candidate for treatment of such conditions as choroidal neovascularization, heart disease, and cancer. Previously, an 18 amino-acid PEDF peptide, P18, was shown to slow cancer growth and blocks ocular angiogenesis. We now report, more potent, practical and safe, modified peptides related to P18, which inhibit angiogenesis, directly kill ovarian cancer cells, and osteosarcoma cell, and exhibit other therapeutic properties. The modified peptides are uniquely suited chemically to be formulated as prodrugs where the latter are attached to particulate carriers, such as nanoparticles, via labile bonds which can be selected to control the rate of release of the modified peptides from the particulate carrier. The modified peptides also have amino acid substitutions that improve potency as compared with the naturally occurring PEDF amino acid sequence. In addition, we now show that these peptides also enhance resistance of the immune system to cancers, directly kill ovarian cancer cells and bone cancer cells, and protect sensitive normal cells, such as kidney cells, or retinal epithelium cells, from toxic effects of chemotherapy. The peptides also are shown to mitigate fibrotic processes and to have immune stimulatory activity.

SUMMARY

Disclosed are modified pigment epithelium-derived factor (PEDF) peptides, particulate carrier prodrugs thereof, and pharmaceutical compositions comprising the peptides or particulate carrier prodrugs. The peptides, particulate carrier prodrugs, and pharmaceutical compositions may be used to treat diseases and disorders that are amenable to treatment with anti-angiogenic agents, anti-tumorigenic agents, anti-fibrotic agents, and immune stimulating agents.

The disclosed peptides are modified peptides comprising an N-terminal carboxyl group. The modified peptides disclosed herein may be described as having a modified amino acid sequence as follows:

(SEQ ID NO: 14)
Z-B-X-AA0-AA1-AA2-AA3-AA4-AA5-AA6-AA7-AA8-AA9-AA10-Y where:
AA0, AA1, AA2, AA3, AA4, AA5, AA6, AA7, AA8, and AA9 are selected from a naturally occurring amino acid, including sarcosine, or beta alanine;
AA0 is absent or present, and when AA0 is present AA0 is selected from sarcosyl and Gly; or beta alanine or beta alaninyl;
AA1 is absent or present, and when AA1 is present AA1 is selected from sarcosyl and Gly;
AA2 is absent or present, and when AA2 is present AA2 optionally is Tyr;
AA3 is Asp or Asn, optionally when AA2 is present;
AA4 is Leu or Val;
AA5 is Tyr or Phe;
AA6 is Arg;
AA7 is Val or Pro;
AA8 is present or absent, and when AA8 is present AA8 is selected from Arg, Pro, or Gln;
AA9 is present or absent, and when AA9 is present AA9 selected from Ser and Ala;
AA10 is absent or present and selected from Ser, Ser-Thr, Ser-Thr-Ser, Ser-Thr-Ser-Pro, and Ser-Thr-Ser-Pro-Thr;
X is absent or present, and when X is present X is selected from the group consisting of acetyl, butyryl, hexanoyl, methoxy-$PEG_{(n)}CO$, hydroxy-$PEG_{(n)}CO$, amino-$PEG_{(n)}CO$, or sarcosyl-amino-$PEG_{(n)}CO$, where n is 3-13, and X is in an amide bond to an amino terminus of AA0, AA1, or AA2;
B is a di-carboxylic acid containing from 4-8 carbon atoms, which may be straight-chain or branched, and B is in a half-amide bond to an amino terminus of X, or -B is in a half-amide bond to an amino terminus of AA0 when X is absent, or B is in a half-amide bond to an amino terminus of AA1 when X and AA0 are absent, or B is in a half-amide bond to an amino terminus of AA2 when X, AA0 and AA1 are absent, or B is in a half-amide bond to an amino terminus of AA3 when X, AA0, AA1, and AA2 are absent, and B may end in a free carboxyl group, or this otherwise free carboxyl group may be in an ester bond to a hydroxyl group of Z;
Z is absent or present, and when Z is present Z is selected from the group consisting of: primary or secondary hydroxyl groups of sugar monomers present on a polymeric carbohydrate carrier; hydroxyl groups of a hydroxyl terminal dendrimer; and primary or secondary hydroxyl groups of acyclic or cyclic amino alcohols having between 4 and 6 carbon atoms and a single primary or secondary amine that is protected through an amide bond or a carbamate bond; and Y is an amide or a substituted amide selected from alkylamide, dialkylamide, and PEG(n)-amide, where n is 4-12.

Also disclosed herein are prodrugs of the foregoing modified peptides in which the free carboxyl group of the disclosed peptides (e.g., a peptide having a formula B-X-AA0-AA1-AA2-AA3-AA4-AA5-AA6-AA7-AA8-AA9-AA10-Y (SEQ ID NO: 14)) is esterified to a free hydroxyl group of a particulate carrier (e.g., a nanoparticle carrier) to form a particulate carrier prodrug of the modified peptides. Optionally, the prodrugs comprise a linker (or a bridge structure, e.g., a peptide having a formula Z-B-X-AA0-AA1-AA2-AA3-AA4-AA5-AA6-AA7-AA8-AA9-AA10-Y (SEQ ID NO:14)) for linking the peptide to a nanoparticle carrier. The linker may comprise a free hydroxyl group and a free amino group (e.g., an amino alcohol linker). As such, the foregoing modified peptides may be esterified to the linker via the free hydroxyl group and the linker may be attached to a nanoparticle carrier via the amino group of the linker and a free hydroxyl group of the nanoparticle carrier forming a carbamate bond or via the free amino group of the linker and a free carboxyl group of the nanoparticle carrier forming an amide bond.

Also disclosed herein are pharmaceutical compositions comprising any of the foregoing modified peptides or particulate carrier prodrugs thereof. The pharmaceutical compositions may be administered to a subject in a treatment method for treating diseases or disorders that are treated by anti-angiogenic agents and/or anti-tumorigenic agents, including but not limited cell proliferative disorders such as cancer, eye disorders and diseases, kidney diseases and disorders, ear diseases and disorders, inflammatory diseases and disorders, diseases or disorders that are exacerbated by immune suppression or fibrosis.

BRIEF DESCRIPTION OF THE FIGURES

FIG. 1. Novel modified peptides and new peptide sequences as exemplified by SEQ ID NOs:1-13. The ED50 (50% effective dose), is the measure of anti-angiogenic potency obtained by quantitative assessment of apoptosis of activated human endothelial cells (EC) as described in FIGS. 3 and 4.

DETAILED DESCRIPTION

Figure 2:
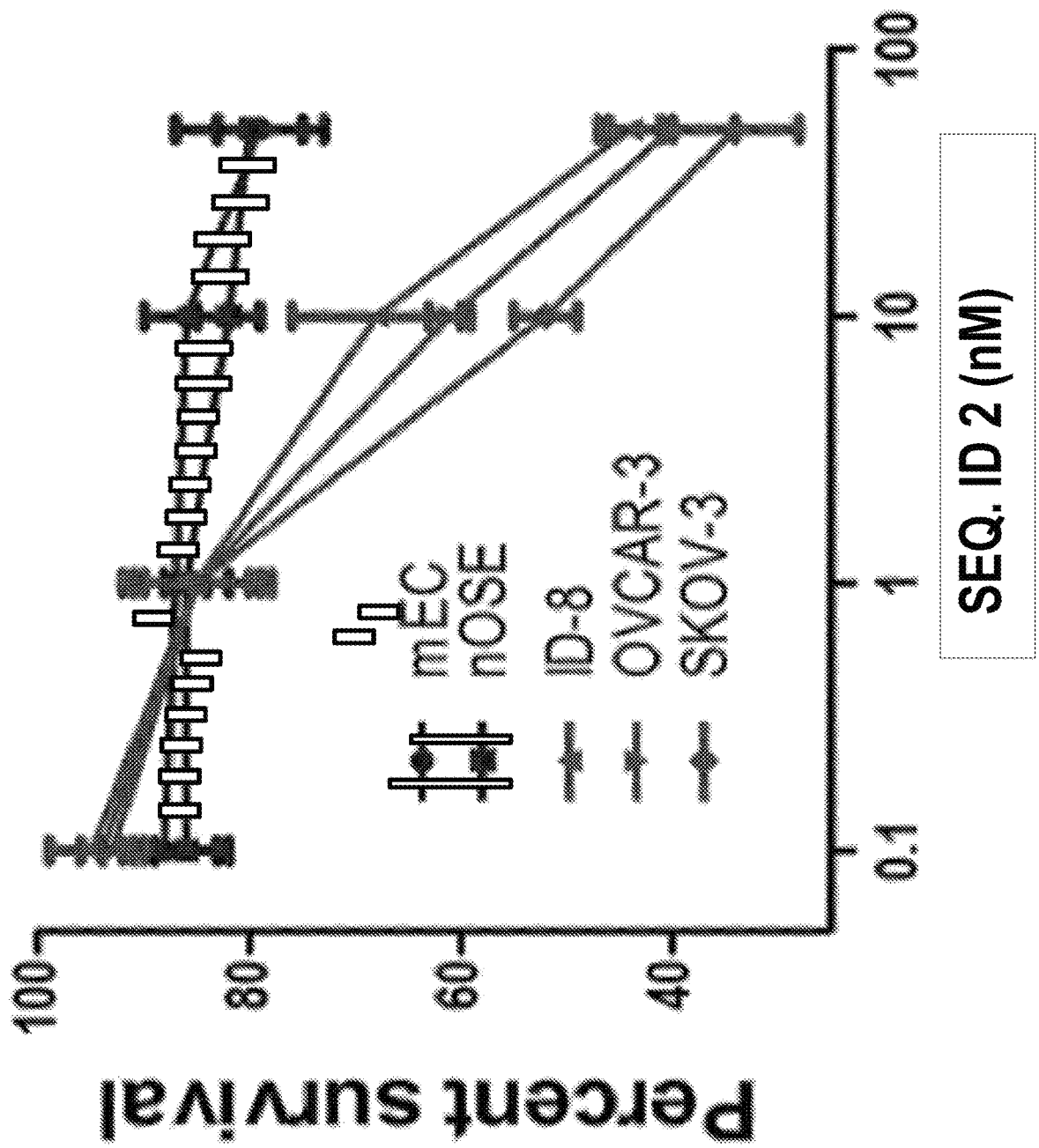
FIG. 2. Selective killing of the ovarian cancer cells by SEQ ID NO:2. Ovarian cancer cells (ID-8, OVCAR-3 and SKOV-3 cell lines), normal ovarian epithelial cells (nOSE) and unstimulated mouse endothelial cells (mEC) were treated with increasing concentrations of SEQ ID NO:2 and survival was measured using a WST assay.

The present invention is described herein using several definitions, as set forth below and throughout the application.

Unless otherwise specified or indicated by context, the terms "a", "an", and "the" mean "one or more." For example, a "peptide" should be interpreted to mean "one or more peptides."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus <10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

As used herein, a "subject" may be interchangeable with a "patient" or "individual" and means an animal, which may be a human or non-human animal, in need of treatment. Non-human animals may include dogs, cats, horses, cows, pigs, sheep, and the like.

A "subject in need thereof" may include a subject having or at risk for developing a cell proliferative disorder such as cancer. Individuals who are treated with the peptides, prodrugs, and pharmaceutical compositions disclosed herein may have cancer or may be at risk for developing cancer, including cancers characterized by solid tumors that may be treated with anti-angiogenic agents and/or anti-tumorigenic agents. The presently disclosed peptides, prodrugs, and pharmaceutical compositions may be utilized to treat cancers or hyperproliferative disorders, which may include, but are not limited to adenocarcinoma, melanoma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

A "subject in need thereof" may include a subject having or at risk for developing an eye disease. The presently disclosed peptides, prodrugs, and pharmaceutical compositions may be utilized to treat eye diseases that are characterized by neovascular retinal disease and that may be treated with anti-angiogenic agents, such as macular degeneration. The presently disclosed peptides, prodrugs, and pharmaceutical compositions may be utilized to treat eye diseases such as diabetic retinopathy or retinopathy of prematurity. The presently disclosed peptides, prodrugs, and pharmaceutical compositions may be utilized to treat eye diseases by administering the disclosed peptide, prodrugs by intravitreal injection.

Macular degeneration is a medical condition predominantly found in elderly adults in which the center of the retina of the eye, otherwise known as the "macula" area of the retina, exhibits thinning, atrophy, and sometimes new blood vessel formation. Although macular degeneration sometimes may affect younger individuals, the term generally refers to "age-related" macular degeneration (i.e., "AMD" or "ARMD"). Advanced AMD has two forms referred to as the "dry" and "wet" forms. The dry form of advanced AMD is characterized by central geographic atrophy, which causes vision loss through the loss of photoreceptors in the central part of the eye (i.e., rods and cones). The wet form of advanced AMD, otherwise referred to as "neovascular" or "exudative" AMD, causes vision loss due to abnormal blood vessel growth in the choriocapillaris, through a retinal layer referred to as "Bruch's membrane." The wet form of AMD ultimately leads to blood and protein leakage below the macula. This bleeding, leaking, and scarring below the macula eventually cause irreversible damage to the photoreceptors and rapid vision loss if left untreated. Until recently, no effective treatments were known for wet macular degeneration. However, new drugs that inhibit angiogenesis (i.e., "anti-angiogenic agents") have been shown to cause regression of the abnormal blood vessels and improvement of vision. In order to be effective, anti-angiogenic agents must be injected directly into the vitreous humor of the eye. The duration of effectiveness of such injections is impractically short for small peptides unless the latter are continuously released from a carrier macromolecule, microparticle, or nanoparticle, for which ester linkage provides controlled rates of release.

The disclosed peptides and compositions thereof may be used in methods for treating or preventing other types of neovascular eye diseases, which may include neovascular eye diseases confined to the anterior portion of the eye, such as the cornea or iris. Infectious and non-infectious keratitis causes corneal clouding by formation of numerous empty neo-capillaries, this is often blinding and no adequate treatments exists beyond corneal transplant. Many larger polypeptides or small charged molecules cannot penetrate corneal outer layers to reach the capillary growth zones. Peptides described here have molecular weights under 1,500 and some have zero or only +1 net charge. With high potency, these can penetrate the cornea topically from eye drops and mitigate corneal clouding.

A "subject in need thereof" may include a subject having or at risk for developing a metabolic disease or disorder such as diabetes. The subject may have diabetes and may benefit from selective cytoprotection of kidney cells from high glucose levels.

A "subject in need thereof" may include a subject having or at risk for developing a kidney disease or disorder. The subject may have diabetes and may benefit from selective cytoprotection of kidney cells from high glucose levels. The subject may be undergoing chemotherapy (e.g., as treatment for cancer) and may benefit from selective cytoprotection of kidney cells from genotoxic stress due to the chemotherapy.

A "subject in need thereof" may include a subject having or at risk for developing an ear disease or disorder. The subject may be undergoing chemotherapy (e.g., as treatment for cancer) and may benefit from treatment and/or prevention of cytotoxic side effects of the chemotherapy.

A "subject in need thereof" may include a subject having or at risk for developing an inflammatory disease or disorder (e.g., chronic inflammatory bowel diseases or disorders such as inflammatory bowel disease). The subject may have diabetes and/or may be undergoing chemotherapy and may benefit from a reduction in reactive oxygen species (ROS) in response to hyperglycemia and chemotherapy.

As used herein, the term "peptide" refers to a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. Typically, the amide linkages of the peptides are formed from an amino group of the backbone of one amino acid and a carboxyl group of the backbone of another amino acid.

As used herein, a peptide is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length>100 amino acids (Garrett & Grisham, Biochemistry, $2^{nd}$ edition, 1999, Brooks/Cole, 110).

The peptides disclosed herein may be modified to include non-amino acid moieties. Modifications may include but are not limited to carboxylation (e.g., N-terminal carboxylation via addition of a di-carboxylic acid having 4-7 straight-chain or branched carbon atoms, such as glutaric acid, succinic acid, adipic acid, and 4,4-dimethylglutaric acid), amidation (e.g., C-terminal amidation via addition of an amide or substituted amide such as alkylamide or dialkylamide), PEGylation (e.g., N-terminal or C-terminal PEGylation via additional of polyethylene glycol), acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The disclosed peptides may exhibit one or more biological functions including anti-angiogenic activity, anti-tumorigenic activity, cytoprotective activity, mitigation of cytotoxicity (e.g., during chemotherapy), and anti-inflammatory activity (e.g., via a reduction in reactive oxygen species (ROS)). Methods for measuring anti-angiogenic activity, anti-tumorigenic activity, cytoprotective activity, mitigation of cytotoxicity, and reduction in reactive oxygen species (ROS) are disclosed herein and are known in the art.

The disclosed peptides may be synthesized by any technique known to those of skill in the art and by methods as disclosed herein. Methods for synthesizing the disclosed peptides may include chemical synthesis of proteins or peptides, the expression of peptides through standard molecular biological techniques, and/or the isolation of proteins or peptides from natural sources. The disclosed peptides thus synthesized may be subject to further chemical and/or enzymatic modification. Various methods for commercial preparations of peptides and polypeptides are known to those of skill in the art.

Reference is made herein to peptides (e.g., PEDF-peptides or variants thereof), polypeptides and pharmaceutical compositions comprising peptides and polypeptides. Exemplary peptides and polypeptides may comprise, consist essentially of, or consist of the amino acid sequence of any of SEQ ID NOs:1-13, or variants of the peptides and polypeptides may comprise, consist essentially of, or consist of an amino acid sequence having at least about 80%, 90%, 95%, 96%, 97%, 98%, or 99% sequence identity to any of SEQ ID NOs:1-13. Variant peptides polypeptides may include peptides or polypeptides having one or more amino acid substitutions, deletions, additions and/or amino acid insertions relative to a reference peptide or polypeptide. Also disclosed are nucleic acid molecules that encode the disclosed peptides and polypeptides (e.g., polynucleotides that encode the peptides or polypeptide of any of SEQ ID NOs:1-13 and variants thereof).

The amino acid sequences contemplated herein may include conservative amino acid substitutions relative to a reference amino acid sequence (e.g., relative to the wild-type human PEDF amino acid sequence. For example, a variant peptide or polypeptide as contemplated herein may include conservative amino acid substitutions and/or non-conservative amino acid substitutions relative to a reference peptide or polypeptide. "Conservative amino acid substitutions" are those substitutions that are predicted to interfere least with the properties of the reference polypeptide, and "non-conservative amino acid substitution" are those substitutions that are predicted to interfere most with the properties of the reference polypeptide. In other words, conservative amino acid substitutions substantially conserve the structure and the function of the reference protein. The following table provides a list of exemplary conservative amino acid substitutions.

TABLE 1

| Original Residue | Conservative Substitution |
| --- | --- |
| Ala | Gly, Ser |
| Arg | His, Lys |

TABLE 1-continued

| Original Residue | Conservative Substitution |
| --- | --- |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain: (a) the structure of the peptide or polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acid substitutions generally disrupt: (a) the structure of the peptide or polypeptide backbone in the area of the substitution, for example, as a beta sheet or alpha helical conformation, (b) the charge or hydrophobicity of the molecule at the site of the substitution, and/or (c) the bulk of the side chain.

Also contemplated herein are peptidomimetics of the disclosed peptides. As disclosed herein, a peptidomimetic is a peptide equivalent characterized as retaining the polarity, three dimensional size and functionality (bioactivity) of its peptide equivalent but where the peptide bonds have been replaced (e.g., by more stable linkages which are more resistant to enzymatic degradation by hydrolytic enzymes). Generally, the bond which replaces the amide bond conserves many of the properties of the amide bond (e.g., conformation, steric bulk, electrostatic character, and possibility for hydrogen bonding). A general discussion of prior art techniques for the design and synthesis of peptidomimetics is provided in "Drug Design and Development", Chapter 14, Krogsgaard, Larsen, Liljefors and Madsen (Eds) 1996, Horwood Acad. Pub, the contents of which are incorporated herein by reference in their entirety. Suitable amide bond substitutes include the following groups: N-alkylation (Schmidt, R. et. al., Int. J. Peptide Protein Res., 1995, 46,47), retro-inverse amide (Chorev, M and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391), which all are incorporated herein by reference in their entireties. The peptides and polypeptide disclosed herein may include peptidomimetic equivalents.

Variants comprising deletions relative to a reference amino acid sequence are contemplated herein. A "deletion" refers to a change in the amino acid or nucleotide sequence that results in the absence of one or more amino acid residues or nucleotides relative to a reference sequence. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation of a reference polypeptide or a 5'-terminal or 3'-terminal truncation of a reference polynucleotide).

Variants comprising fragment of a reference amino acid sequence are contemplated herein. A "fragment" is a portion of an amino acid sequence or a polynucleotide which is identical in sequence to but shorter in length than a reference sequence. A fragment may comprise up to the entire length of the reference sequence, minus at least one nucleotide/amino acid residue. For example, a fragment may comprise from 5 to 1000 contiguous nucleotides or contiguous amino acid residues of a reference polynucleotide or reference polypeptide, respectively. In some embodiments, a fragment may comprise at least 5, 10, 15, 20, 21, 22, 23, 24, 25, 26, 27, 28, 29, 30, 40, 50, 60, 70, 80, 90, 100, 150, 250, or 500 contiguous nucleotides or contiguous amino acid residues of a reference polynucleotide or reference polypeptide, respectively. Fragments may be preferentially selected from certain regions of a molecule. The term "at least a fragment" encompasses the full length polynucleotide or full length polypeptide.

Variants comprising insertions or additions relative to a reference sequence are contemplated herein. The words "insertion" and "addition" refer to changes in an amino acid or sequence resulting in the addition of one or more amino acid residues. An insertion or addition may refer to 1, 2, 3, 4, 5, 10, 20, 30, 40, 50, 60, 70, 80, 90, 100, 150, or 200 amino acid residues.

Fusion proteins also are contemplated herein. The disclosed polypeptides may comprise fusion proteins. A "fusion protein" refers to a protein formed by the fusion of at least one peptide or variant thereof as disclosed herein to at least one molecule of a heterologous protein (or fragment or variant thereof). The heterologous protein(s) may be fused at the N-terminus, the C-terminus, or both termini of the peptides or variants thereof. A fusion protein comprises at least a fragment or variant of the heterologous protein and at least a fragment or variant of the presently disclosed peptides, which are associated with one another, preferably by genetic fusion (i.e., the fusion protein is generated by translation of a nucleic acid in which a polynucleotide encoding all or a portion of the heterologous protein is joined in-frame with a polynucleotide encoding all or a portion of the disclosed peptides or variants thereof). The heterologous protein and peptide, once part of the fusion protein, may each be referred to herein as a "portion", "region" or "moiety" of the fusion protein (e.g., a "a heterologous protein portion" or a "PEDF peptide portion").

"Homology" refers to sequence similarity or, interchangeably, sequence identity, between two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant" of a particular polypeptide sequence may be defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" may have substantially the same functional activity as a reference polypeptide. For example, a variant may exhibit or more biological activities associated with PEDF. "Substantially isolated or purified" nucleic acid or amino acid sequences are contemplated herein. The term "substantially isolated or purified" refers to nucleic acid or amino acid sequences that are removed from their natural environment, and are at least 60% free, preferably at least 75% free, and more preferably at least 90% free, even more preferably at least 95% free from other components with which they are naturally associated.

A "composition comprising a given polypeptide" refers broadly to any composition containing the given amino acid sequence. The composition may comprise a dry formulation or an aqueous solution. The compositions may be stored in any suitable form including, but not limited to, freeze-dried form and may be associated with a stabilizing agent such as a carbohydrate. The compositions may be aqueous solution containing salts (e.g., NaCl), detergents (e.g., sodium dodecyl sulfate; SDS), and other components (e.g., Denhardt's solution, dry milk, salmon sperm DNA, and the like).

The disclosed pharmaceutical composition may comprise the disclosed peptides, polypeptides, variants at any suitable dose. Suitable doses may include, but are not limited to, about 0.01 µg/dose, about 0.05 µg/dose, about 0.1 µg/dose, about 0.5 µg/dose, about 1 µg/dose, about 2 µg/dose, about 3 µg/dose, about 4 µg/dose, about 5 µg/dose, about 10 µg/dose, about 15 µg/dose, about 20 µg/dose, about 25

µg/dose, about 30 µg/dose, about 35 µg/dose, about 40 µg/dose, about 45 µg/dose, about 50 µg/dose, about 100 µg/dose, about 200 µg/dose, about 500 µg/dose, or about 1000 µg/dose.

The disclosed peptides, polypeptides, or variants thereof may be administered at any suitable dose level. In some embodiments, a subject in need thereof is administered a peptide, polypeptide, or variant thereof at a dose level of from about 1 ng/kg up to about 2000 ng/kg. In some embodiments, the peptide, polypeptide, or variant thereof is administered to the subject in need thereof at a dose level of at least about 1 ng/kg, 2 ng/kg, 5 ng/kg, 10 ng/kg, 20 ng/kg, 50 ng/kg, 100 ng/kg, 200 ng/kg, 500 ng/kg, 1000 ng/kg or 2000 ng/kg. In other embodiments, the peptide, polypeptide, or variant thereof is administered to the subject in need thereof at a dose level of less than about 2000 ng/kg, 1000 ng/kg, 500 ng/kg, 200 ng/kg, 100 ng/kg, 50 ng/kg, 20 ng/kg, 10 ng/kg, 5 ng/kg, 2 ng/kg, or 1 ng/kg. In further embodiments, the peptide, polypeptide, or variant thereof is administered to a subject in need thereof within a dose level range bounded by any 1 ng/kg, 2 ng/kg, 5 ng/kg, 10 ng/kg, 20 ng/kg, 50 ng/kg, 100 ng/kg, 200 ng/kg, 500 ng/kg, 1000 ng/kg or 2000 ng/kg.

The disclosed peptides, polypeptides, or variants thereof may be administered under any suitable dosing regimen. Suitable dosing regimens may include, but are not limited to, daily regimens (e.g., 1 dose/day for 1, 2, 3, 4, 5, 6, 7 or more days), twice daily regimens (e.g., 2 doses/day for 1, 2, 3, 4, 5, 6, 7 or more days), and thrice daily regiments (e.g., 3 doses/day for 1, 2, 3, 4, 5, 6, 7 or more days). Suitable regiments also may include dosing every other day, 3 times/week, once a week, for 1, 2, 3, 4, or more weeks.

The peptides and prodrugs utilized in the methods disclosed herein may be formulated as a pharmaceutical composition for delivery via any suitable route (e.g. parenteral or intravitreal routes). As such, pharmaceutical compositions comprising the peptides and prodrugs may be adapted for administration by any appropriate route, for example intravitreal or intraperitoneal, with the intention of local confinement, and parenteral (including subcutaneous, intramuscular, intravenous or intradermal) route. Such formulations may be prepared by any method known in the art of pharmacy, for example by bringing into association the active ingredient with suitable carrier(s) or excipient(s). In some embodiments, the prodrug carrier-bound forms described herein may be intended for less frequent dosing ranging from once weekly to once monthly to once per 2 months or less frequently. Pharmaceutical compositions adapted for parenteral administration include aqueous and non-aqueous sterile injection solutions which may contain anti-oxidants, buffers, bacteriostats and solutes which render the formulation isotonic with bodily fluid of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use.

Anti-Angiogenic and Anti-Tumorigenic Peptides

The disclosed peptides may be described as modified peptides comprising an N-terminal carboxyl group. The modified peptides disclosed herein may be described as having a modified amino acid sequence as follows:

(SEQ ID NO: 14)
Z-B-X-AA0-AA1-AA2-AA3-AA4-AA5-AA6-AA7-AA8-AA9-AA10-Y where:

AA0, AA1, AA2, AA3, AA4, AA5, AA6, AA7, AA8, and AA9 are selected from a naturally occurring amino acid, including sarcosine, or beta-alanine;

AA0 is absent or present, and when AA0 is present AA0 is selected from sarcosyl and Gly; or beta-alanyl;

AA1 is absent or present, and when AA1 is present AA1 is selected from sarcosyl and Gly;

AA2 is absent or present, and when AA2 is present AA2 optionally is Tyr;

AA3 is Asp or Asn, optionally when AA2 is present;

AA4 is Leu or Val;

AA4 is Leu;

AA5 is Tyr or Phe;

AA6 is Arg;

AA7 is Val or Pro;

AA8 is present or absent, and when AA8 is present AA8 is selected from Arg, Pro, or Gln;

AA9 is present or absent, and when AA9 is present AA9 selected from Ser and Ala;

AA10 is absent or present and selected from Ser, Ser-Thr, Ser-Thr-Ser, Ser-Thr-Ser-Pro, and Ser-Thr-Ser-Pro-Thr;

X is absent or present, and when X is present X is selected from the group consisting of acetyl, butyryl, hexanoyl, methoxy-PEG$_{(n)}$CO, hydroxy-PEG$_{(n)}$CO, amino-PEG$_{(n)}$CO, or sarcosyl-amino-PEG$_{(n)}$CO, where n is 3-13, and X is in an amide bond to an amino terminus of AA0, AA1, or AA2;

B is a di-carboxylic acid containing from 4-8 carbon atoms, which may be straight-chain or branched, and B is in a half-amide bond to an amino terminus of X, or-B is in a half-amide bond to an amino terminus of AA0 when X is absent, or B is in a half-amide bond to an amino terminus of AA1 when X and AA0 are absent, or B is in a half-amide bond to an amino terminus of AA2 when X, AA0 and AA1 are absent, or B is in a half-amide bond to an amino terminus of AA3 when X, AA0, AA1, and AA2 are absent, and B may end in a free carboxyl group, or this otherwise free carboxyl group may be in an ester bond to a hydroxyl group of Z;

Z is absent or present, and when Z is present Z is selected from the group consisting of: primary or secondary hydroxyl groups of sugar monomers present on a polymeric carbohydrate carrier; hydroxyl groups of a hydroxyl terminal dendrimer; and primary or secondary hydroxyl groups of acyclic or cyclic amino alcohols having between 4 and 6 carbon atoms and a single primary or secondary amine that is protected through an amide bond or a carbamate bond; and Y is an amide or a substituted amide selected from alkylamide, dialkylamide, and PEG$_{(n)}$-amide, where n is 4-12.

The disclosed modified peptides typically include a free N-terminal carboxyl group. For example, the modified peptides may be formed by adding a di-carboxylic acid to an N-terminal amino group to form a half-amide bond. Suitable di-carboxylic acids may include, but are not limited to di-carboxylic acids comprising 4-7 straight-chain or branched carbon atoms such as glutaric acid, succinic acid, adipic acid, and 4,4-dimethylglutaric acid.

In some embodiments, the modified peptide may comprise a modified amino acid sequence as follows: B-X-AA1-AA2-AA3-AA4-AA5-AA6-AA7-AA8-AA9-Y (SEQ ID NO:14), where X, AA1, AA2, AA3, AA4, AA5, AA6, AA7, AA8, AA9, and Y are as defined above. In other embodiments, the modified peptide may comprise a modified amino acid sequence as follows: B-sarcosyl-AA1-AA2-AA3-AA4-AA5-AA6-AA7-AA8-AA9-Y (SEQ ID NO:14), where B, AA1, AA2, AA3, AA4, AA5, AA6, AA7, AA8, AA9, and Y are as defined above. In further embodiments, the modified peptide may comprise a modified amino acid sequence as follows: Z-B-sarcosyl-AA1-AA2-AA3-AA4-AA5-AA6-AA7-AA8-AA9-amide (SEQ ID NO:14), where AA1, AA2, AA3, AA4, AA5, AA6, AA7, AA8, and AA9 are as defined above. In even further embodiments, the modified peptide may comprise a modified amino acid sequence as follows: the glutaryl-sarcosyl-Gly-Tyr-AA3-Leu-Tyr-Arg-Val-AA8-AA9-amide (SEQ ID NO:14), where AA3, AA8, and AA9 are as defined above.

In some embodiments, the modified peptide may comprise an N-terminal group selected from glutaryl; adipoyl, suberoyl, 4,4-dimetlyglutaryl-Sar; adipoyl-Sar-PEG(4-12); 4,4-dimetlyglutaryl-Sar-PEG(4-12)-Sar; or PEG-(4-13)-CO). In other embodiments, the modified peptide may comprise a modified amino acid sequence having a N-terminal group selected from glutaryl-sarcosyl or 4,4-dimetlyglutaryl-sarcosyl. In further embodiments, the modified peptide may comprise a modified amino acid sequence as follows: glutaryl-sarcosyl-AA1-AA2-AA3-AA4-AA5-AA6-AA7-AA8-AA9-amide (SEQ ID NO:14) or adipoyl-sarcosyl-AA1-AA2-AA3-AA4-AA5-AA6-AA7-AA8-AA9-amide (SEQ ID NO:14), or adipoyl-sarcosyl-AA2-AA3-AA4-AA5-AA6-AA7-AA8-AA9-amide (SEQ ID NO:14), or suberoyl-AA3-AA4-AA5-AA6-AA7-AA8-AA9-amide (SEQ ID NO:14) where AA1, AA2, AA3, AA4, AA5, AA6, AA7, AA8, and AA9 are as defined above.

Specifically, the disclosed peptides may include modified peptides comprising a modified amino acid sequence selected from: glutaryl-sarcosyl-Gly-Tyr-Asp-Leu-Tyr-Arg-Val-Arg-Ser-amide (i.e., SEQ ID NO:2); and glutaryl-sarcosyl-Gly-Tyr-Asn-Leu-Tyr-Arg-Val-Arg-Ser-amide (i.e., SEQ ID NO:4), where a charged amino acid in a reference sequence (e.g., PEDF) is replaced with a neutral amino acid (sarcosyl-NH-PEG(4)CO-Sar-Tyr-Asn-Leu-Tyr-Arg-Val-Arg-Ser-amide (i.e., SEQ ID NO:6)). In addition, the disclosed peptides also include truncation and modifications near and at the C-terminus as in glutaryl-sarcosyl-Tyr-Asn-Leu-Tyr-Arg-Val-Pro-ethylamide (SEQ ID NO:8) (see also SEQ ID NO:10 and SEQ ID NO:12), where a second charged Arg residue is also replaced by a neutral one, Pro, yielding a smaller, more potent peptide, and glutaryl-sarcosyl-Tyr-Asn-Leu-Tyr-Arg-Val-Gln-Ser-amide (SEQ ID NO:9) where the Arg is replaced by Gln, without truncation, again with enhanced potency Prodrugs of the disclosed peptides also are contemplated herein. In some embodiments, prodrugs of the disclosed peptides may comprise any of the disclosed peptides and a microparticle carrier or nanoparticle carrier having a free hydroxyl, where the N-terminal carboxyl group of the peptide is esterified to the free hydroxyl group of the carrier in order to form a carrier prodrug of the disclosed peptides.

In other embodiments of the prodrugs, the prodrugs may comprise: (a) any of the disclosed peptides; (b) a linker having a free hydroxyl group and a free amino group (e.g., an amino alcohol linker) for linking the peptides to the carriers (i.e., microparticle carriers and/or nanoparticle carriers); and (c) a carrier having a free hydroxyl group or a free carboxyl group. In this embodiment, the prodrug is prepared by (a) esterifying the peptide to the free hydroxyl group of the linker; and by (b) attaching the linker to the carrier via the amino group of the linker and a free hydroxyl group of the carrier to form a carbamate bond, or by attaching the amino group of the linker and a free carboxyl group of the carrier to form an amide bond. Suitable linkers may include, but are not limited to amino-n-butoxy, amino-ethoxyethyl-oxy, amino-piperidyl(3, or 4)-oxy, amino-pyrrolidinyl(3)-oxy, amino-benzyloxy, BOC-aminoethylamido-valeric acid (4)-oxy, amino-cyclohexyl (3, or 4)-oxy, and amino-cyclopentyl (3)-oxy.

The carriers of the prodrug may be microparticle carriers and/or nanoparticle carriers. For example, the carriers of the prodrug may have an average effective diameter that is less than about 0.2 microns (e.g., when the carriers are formulated for intravitreal administration). In some embodiments, the carriers of the prodrug may have an average effective diameter that ranges from 0.05 microns to 20 microns (e.g., when the carriers are formulated for intraperitoneal administration). In some embodiments, the carriers are nanoparticle carriers having an average effective diameter that is less than about 1 micron (e.g., an average effective diameter that ranges from 0.01 microns to 1 micron). The carrier typically comprises a polymeric material having terminal hydroxyl groups and/or terminal carboxyl groups. In some embodiments, the carriers comprise dendrimers having terminal hydroxyl groups and/or terminal carboxyl groups. In further embodiments, the carriers comprise dextran and/or hyaluronic acid, and optionally the dextran or hyaluronic acid is crosslinked and/or condensed. Optionally, the carriers may be optically transparent or substantially optically transparent (e.g., when the carriers are used in preparing a prodrug for intravitreal administration). For example, a transparent or substantially transparent carriers may absorb and reflect less than about 10%, 9%, 8%, 7%, 6%, 5%, 4%, 3%, 2%, or 1% of incident light and/or may have a total transmittance of at least about 90%, 91%, 92%, 93%, 94%, 95%, 96%, 97%, 98%, or 99% of incident light.

The modified peptides disclosed herein and the prodrugs thereof may be formulated as pharmaceutical compositions for use in treating and/or preventing diseases or disorders that are amenable to treatment by anti-angiogenic agents and/or anti-tumorigenic agents. As such, the pharmaceutical compositions may be administered to a subject in order to inhibit angiogenesis and/or tumorigenesis in the subject.

The disclosed methods may include administering to a subject an effective amount of a peptide, prodrug, or pharmaceutical composition to treat and/or prevent a disease and/or disorder. As used herein, the phrase "effective amount" shall mean that drug dosage that provides the specific pharmacological response for which the drug is administered in a significant number of subjects in need of such treatment. An effective amount of a drug that is administered to a particular subject in a particular instance will not always be effective in treating the conditions/diseases described herein, even though such dosage is deemed to be a therapeutically effective amount by those of skill in the art.

The disclosed methods may include administering to a subject an effective amount of a peptide, prodrug, or pharmaceutical composition for inhibiting angiogenesis and/or tumorigenesis relative to a control. In some embodiments, angiogenesis and/or tumorigenesis is inhibited by at least 10%, at least 25%, at least 50%, at least 75%, at least 90%, or at least 95% in a treated sample relative to an untreated control sample.

Illustrative Embodiments

The following embodiments are illustrative and should not be interpreted to limit the scope of the claimed subject matter.

Embodiment 1. A modified peptide comprising an N-terminal carboxyl group and a modified amino acid sequence as follows:

```
                                            (SEQ ID NO: 14)
Z-B-X-AA0-AA1-AA2-AA3-AA4-AA5-AA6-AA7-AA8-AA9-

AA10-Y
``` wherein:
AA0, AA1, AA2, AA3, AA4, AA5, AA6, AA7, AA8, and AA9 are selected from a naturally occurring amino acid, including sarcosine, or beta alanine;
AA0 is absent or present, and when AA0 is present AA0 is selected from sarcosyl and Gly; or beta alaninyl;
AA1 is absent or present, and when AA1 is present AA1 is selected from sarcosyl and Gly;
AA2 is Tyr;
AA2 is absent or present, and when AA2 is present AA3 is selected from Asp or Asn;
AA3 is Asp or Asn;
AA4 is Leu or Val;
AA5 is Tyr or Phe;
AA6 is Arg;
AA7 is Val or Pro;
AA8 is present or absent, and when AA8 is present AA8 is selected from Arg, Pro, or Gln;
AA9 is present or absent, and when AA9 is present AA9 selected from Ser and Ala;
AA10 is absent or present and selected from Ser, Ser-Thr, Ser-Thr-Ser, Ser-Thr-Ser-Pro, and Ser-Thr-Ser-Pro-Thr;
X is absent or present, and when X is present X is selected from the group consisting of acetyl, butyryl, hexanoyl, methoxy-PEG$_{(n)}$CO, hydroxy-PEG$_{(n)}$CO, amino-PEG$_{(n)}$CO, or sarcosyl-amino-PEG(n)CO, where n is 3-13, and X is in an amide bond to an amino terminus of AA0, AA1, or AA2;
B is a di-carboxylic acid containing from 4-8 carbon atoms, which may be straight-chain or branched, and B is in a half-amide bond to an amino terminus of X, or-B is in a half-amide bond to an amino terminus of AA0 when X is absent, or B is in a half-amide bond to an amino terminus of AA1 when X and AA0 are absent, or B is in a half-amide bond to an amino terminus of AA2 when X, AA0 and AA1 are absent, or B is in a half-amide bond to an amino terminus of AA3 when X, AA0, AA1, and AA2 are absent; and B may end in a free carboxyl group, or this otherwise free carboxyl group may be in an ester bond to a hydroxyl group of Z;
Z is absent or present, and when Z is present Z is selected from the group consisting of: primary or secondary hydroxyl groups of sugar monomers present on a polymeric carbohydrate carrier; hydroxyl groups of a hydroxyl terminal dendrimer; and primary or secondary hydroxyl groups of acyclic or cyclic amino alcohols having between 4 and 6 carbon atoms and a single primary or secondary amine that is protected through an amide bond or a carbamate bond; and
Y is an amide or a substituted amide selected from alkylamide, dialkylamide, and PEG(n)-amide, where n is 4-12.

Embodiment 2. The modified peptide of embodiment 1 comprising a modified amino acid sequence as follows: B-AA0-AA1-AA2-AA3-AA4-AA5-AA6-AA7-AA8-AA9-Y (SEQ ID NO:14).

Embodiment 3. The modified peptide of embodiment 1 or 2, wherein B is adipic acid or glutaric acid in half amide bond to AA0, or B is in a half-amide bond to an amino terminus of AA1 when AA0 is absent, or B is in a half-amide bond to an amino terminus of AA2 when AA0 and AA1 are absent.

Embodiment 4. The modified peptide of any of the foregoing embodiments wherein AA2-AA3-AA4-AA5-AA6-AA7-AA8-AA9 is Tyr-Asn-Leu-Tyr-Arg-Val-Arg-Ser (SEQ ID NO:14).

Embodiment 5. The modified peptide of any of the foregoing embodiments wherein AA2-AA3-AA4-AA5-AA6 is Tyr-Asn-Leu-Tyr-Arg (SEQ ID NO:14).

Embodiment 6. The modified peptide of any of the foregoing embodiments wherein AA7 is Val or Pro-ethylamide when AA6 is the C-terminal amino acid of the peptide.

Embodiment 7. The modified peptide of any of the foregoing embodiments wherein AA7 is Val and AA8 is Pro-ethylamide when AA8 is the C-terminal amino acid of the peptide.

Embodiment 8. The modified peptide of any of the foregoing embodiments wherein AA7-AA8-AA9 is Val-Gln-Ser.

Embodiment 9. The modified peptide of any of the foregoing embodiments wherein Y is amide or ethylamide.

Embodiment 10. The modified peptide of any of the foregoing embodiments wherein the peptide does not have an Arg at position AA8.

Embodiment 11. The modified peptide of any of the foregoing embodiments having a N-terminal moiety, which may be substituent B, selected from succinic acid, glutaric acid, adipic acid, and suberic acid.

Embodiment 12. The modified peptide of any of the foregoing embodiments comprising a modified amino acid sequence as follows: sarcosyl-AA1-AA2-AA3-AA4-AA5-AA6-AA7-AA8-AA9-Y (SEQ ID NO:14).

Embodiment 13. The modified peptide of any of the foregoing embodiments comprising a modified amino acid sequence as follows: glutaryl-sarcosyl-AA1-AA2-AA3-AA4-AA5-AA6-AA7-AA8-AA9-amide (SEQ ID NO:14).

Embodiment 14. The modified peptide of any of the foregoing embodiments comprising a modified amino acid sequence as follows: glutaryl-sarcosyl-Gly-Tyr-AA3-Leu-Tyr-Arg-Val-AA8-AA9-amide (SEQ ID NO:14).

Embodiment 15. The modified peptide of any of the foregoing embodiments comprising a modified amino acid sequence: glutaryl-sarcosyl-Gly-Tyr-Asp-Leu-Tyr-Arg-Val-Arg-Ser-amide (i.e., SEQ ID NO:2).

Embodiment 16. The modified peptide of any of the foregoing embodiments comprising a modified amino acid sequence: glutaryl-sarcosyl-Gly-Tyr-Asn-Leu-Tyr-Arg-Val-Arg-Ser-amide (i.e., SEQ ID NO:4).

Embodiment 17. The modified peptide of any of the foregoing embodiments comprising a modified amino acid sequence: adipoyl-sarcosyl-Tyr-Asn-Leu-Tyr-Arg-Val-Arg-Ser-amide (i.e., SEQ ID NO:11).

Embodiment 18. The modified peptide of any of the foregoing embodiments comprising a modified amino acid sequence: glutaryl-sarcosyl-Gly-Tyr-Asn-Leu-Tyr-Arg-Val-Pro-ethylamide (i.e., SEQ ID NO: 8).

Embodiment 19. The modified peptide of any of the foregoing embodiments comprising a modified amino acid sequence: adipoyl-sarcosyl-Tyr-Asn-Leu-Tyr-Arg-Val-Pro-ethylamide (i.e., SEQ ID NO: 10).

Embodiment 20. The modified peptide of any of the foregoing embodiments comprising a modified amino acid sequence disclosed in FIG. 1.

Embodiment 21. A prodrug of any of the foregoing modified peptides comprising a modified amino acid sequence as follows: Z-B-AA0-AA1-AA2-AA3-AA4-AA5-AA6-AA7-AA8-AA9-Y (SEQ ID NO:14) where Z is an amido or carbamato alcohol in ester bond linkage to B, and Z is in amide or carbamate bond linkage to a carboxyl group or a hydroxyl group of a polymeric carrier particle.

Embodiment 22. A prodrug of any of the modified peptides of embodiments 1-20 in which the N-terminal carboxyl group of the peptide is esterified to a free hydroxyl group of a particulate carrier.

Embodiment 23. A prodrug of any of the modified peptides of embodiments 1-20 in which the prodrug further comprises an amino alcohol linker and the peptide is esterified to a free hydroxyl group of the linker, and the linker is attached to a particulate carrier via the amino group of the linker and a free hydroxyl group of the particulate carrier forming a carbamate bond or via the amino group of the linker and a free carboxyl group of the particulate carrier forming an amide bond, and optionally the linker is selected from the group consisting of amino-n-butoxy, amino-ethoxyethyloxy, amino-piperidyl(3, or 4)-oxy, amino-pyrrolidinyl(3)-oxy, amino-benzyloxy, BOC-aminoethylamido-valeric acid (4)-oxy, amino-cyclohexyl (3, or 4)-oxy, and amino-cyclopentyl (3)-oxy.

Embodiment 24. The prodrug of any of embodiments 21-23, wherein the particulate carrier comprises dendrimers having terminal hydroxyl or carboxyl groups.

Embodiment 25. The prodrug of any of embodiments 21-24, wherein the particulate carrier comprises dextrin, dextran, or hyaluronic acid.

Embodiment 26. The prodrug of embodiment 25, wherein the dextrin, dextran, or hyaluronic acid is crosslinked and/or condensed.

Embodiment 27. A pharmaceutical composition comprising the modified peptides of any of embodiments 1-20 or prodrugs thereof, optionally as the prodrugs of any of embodiments 21-26, together with a pharmaceutical acceptable carrier, diluent, or excipient.

Embodiment 28. A method of treating and/or preventing cancer in a subject in need thereof, the method comprising administering the composition of embodiment 27 to the subject.

Embodiment 29. The method of embodiment 28, wherein the subject has ovarian cancer or colon cancer and the pharmaceutical composition is administered by parenteral administration.

Embodiment 30. A method of treating and/or preventing cancer in a subject having immune suppression characterized by elevated PD-L1, the method comprising administering the composition of embodiment 27 to the subject.

Embodiment 31. The method of embodiment 30, wherein the subject has cancer types known to be responsive to immune stimulation therapy such as but not limited to melanoma, non-small cell lung cancer, bladder cancer, renal cell carcinoma, and oral squamous cell carcinoma, and the pharmaceutical composition is administered by parenteral administration.

Embodiment 32. A method of treating and/or preventing infectious disease in a subject having immune suppression characterized by elevated PD-L1, the method comprising administering the composition of embodiment 27 to the subject.

Embodiment 33. A method of treating and/or preventing an eye disease or disorder in a subject in need thereof, the method comprising administering the composition of embodiment 27 to the subject.

Embodiment 34. The method of embodiment 33, wherein the eye disease is a neovascular retinal disease.

Embodiment 35. The method of embodiment 34, wherein the neovascular retinal disease is macular degeneration.

Embodiment 36. The method of embodiment 33, wherein the eye disease or disorder is diabetic retinopathy or retinopathy of prematurity.

Embodiment 37. The method of embodiment 33, wherein the pharmaceutical composition is formulated for topical administration as eye drops for treating corneal (keratitis), iris, or retinal neovascular disease.

Embodiment 38. A method of treating and/or preventing a kidney disease or disorder in a subject in need thereof, the method comprising administering the pharmaceutical composition of embodiment 27 to the subject.

Embodiment 39. The method of embodiment 38, wherein the subject has diabetes and the method protects kidney cells from high glucose.

Embodiment 40. The method of embodiment 38, wherein the subject is undergoing chemotherapy and the method protects kidney cells from genotoxic stress.

Embodiment 41. A method of treating and/or preventing an ear disease or disorder in a subject in need thereof, the method comprising administering the pharmaceutical composition of embodiment 27 to the subject.

Embodiment 42. The method of embodiment 41, wherein the subject is undergoing chemotherapy and the method treats and/or prevents cytotoxicity.

Embodiment 43. Any 8-10 amino acid anti-angiogenic peptide with C-terminal amide or ethylamide which is N-terminally capped as half-amide with adipic acid, which esterified to an amino alcohol, where the latter is further attached as a carbamate or amide to OH groups or carboxyl groups of a polymeric carrier, a specific example being: amino-alkoxy-adipoyl-Gly-Val-DalloI-Ser-Gln-Ile-Arg-Pro-ethylamide in carbamate linkage to a condensed dextran hydrogel.

EXAMPLES

The following Examples are illustrative and are not intended to limit the scope of the claimed subject matter.

Example 1—Anti-Angiogenic PEDF Peptides and their Ester Pro-Drugs for Treating Cancer and Eye Diseases Abstract Cancer growth, and retina diseases that cause blindness are both driven by excessive formation of the new capillaries (angiogenesis). Ovarian cancer (OvCa) initially responds to chemotherapy but resistant cells remain and re-grow. Chemotherapy for OvCa is typically administered through intravenous (IV) route, but is more effective when delivered locally (intraperitoneally, IP). Adding an anti-angiogenic agent Avastin, which neutralizes vascular endothelial growth factor (VEGF), can slow relapse; however, it is not amenable to local IP delivery and is typically given IV. Longer remission caused by Avastin is counterbalanced by its VEGF-related toxicities, which include intestinal perforation, and hypertension. Avastin and other anti-VEGF proteins are also used to alleviate exudative macular degeneration, where excessive pathologic capillary sprouting beneath the retina destroys retinal layers. None of these proteins is suited for sustained release formulation, and their rapid clearance from the eye necessitates burdensome monthly intraocular injections. We invented non-toxic small anti-angiogenic peptides that mimic activity of the natural angiogenesis inhibitor Pigment Epithelium-Derived Factor (PEDF). We have previously patented an 18 amino-acid PEDF peptide, P18, which slows cancer growth and blocks ocular angiogenesis. (See U.S. Pat. Nos. 9,096,689; 8,198,406; 7,723,313; 7,105,496; 6,919,309; and 6,797,691; the contents of which are incorporated herein by reference in their entireties).

We now report, more potent, practical and safe, 8-10 amino acid peptides related to or derived from P18, which inhibit angiogenesis and directly kill ovarian cancer cells. The disclosed peptides include significant chemical and amino acid sequence modifications. The same peptides inhibit capillary sprouting from tissue explants prepared from mouse choroid; these results imply efficacy vs. eye disease. These peptides are appended with novel linking groups to facilitate metastable chemical attachment to nanoparticles for slow (>1 month) release for extended therapeutic effect when given IP, intra-cranially or intra-vitreally. Our new peptides may be conjugated to nanoparticles, which are designed to anchor at their site of delivery with specified controlled drug release rates, which can be adjusted through manipulating particle size and charge, and through amino alcohol bridging ester groups. This will (1) extend time between eye injections with improved clinical results in AMD, and (2) enable local treatment of OvCa and other cancers for more effective therapy.

Advantages

1. Anti-angiogenic adjuvant therapy delays relapse in ovarian cancer (OvCa) patients, but is based on agents whose anti-VEGF mechanism cause grave systemic toxicities. Our peptide anti-angiogenics are both effective and safe because they mimic the action of endogenous, locally expressed anti-angiogenic protein (PEDF) whose levels dwindle in cancer and angiogenic eye disease.

2. OvCa patients receive chemotherapy by intravenous (IV) injections, but remission is more lasting with chemotherapy delivered directly the existing anti-VEGF agents require IV administration, and are not locally concentrated or amenable to controlled release. Our peptide anti-angiogenics are specifically designed for slow local intraperitoneal release from carrier nano-devices.

3. Unexpectedly, in addition to eliminating neovasculature, our modified PEDF peptides kill OvCa cells but not normal ovarian cells.

4. Because our peptides use a mechanism distinct from VEGF inhibition, they can produce additive or synergistic results, and thus superior clinical outcomes, in combination with existing anti-VEGFs.

5. Anti-VEGF proteins currently are used to treat wet macular degeneration and other neovascular eye diseases by intraocular injection. Their half-lives in the eye are between 4-6 days, they must be re-injected at 1-2 months intervals. This number of intraocular injections is burdensome, painful, and poses risks of retinal detachment, corneal damage and infection. Our slow-release peptide formulations use linkage to transparent nanoparticles, with significant adherence to vitreous humor until the majority of the drug is released. This will give sustained action so that injections can be less frequent, ideally once every 2-4 months.

6. In our technology, intraperitoneal (IP) drug exposure is prolonged by use of larger particles and/or by the adherence of the conjugates in smaller particles to poly-anionic mucosa/ECM or vitreous humor via surface display of multiple positively charged peptides, in those cases of peptides having net positive charge (SEQ ID NO:4). This charge-based anchoring allows prolonged drug release. Our delivery system offers modes of local body space confinement using both size and charge, thus it is broadly applicable to cancer, endometriosis and eye disease. In cases where the vitreous gel of the eye has been surgically removed (vitrectomy) the slow delivery of carrier-linked peptides can be enabled through their formulation with pharmaceutical grade hyaluronic acid gels for intraocular use such as Healon® ophthalmic viscoelastics (OVDs). In the peritoneum our amino ester prodrug peptides can be linked as amides to maleic anhydride activated carriers such as Gantrez™ polymers approved for intraperitoneal administration.

Description

PEDF (Pigment Epithelial-Derived Factor) loss is a hallmark of malignancy/poor prognosis in human disease including advanced OvCa. PEDF, made in the retina, and in many tissues is a major inhibitor of both tumor and ocular angiogenesis and is reduced in eyes with neovascular disease. Importantly, added PEDF significantly impedes the cancer growth in preclinical models. PEDF's anti-angiogenic, pro-apoptotic activity was localized to its N-terminal 34 amino acid fragment. The anti-angiogenic, pro-apoptotic activity was further refined to an 18 amino acid peptide (P18), (see U.S. Pat. No. 8,198,406) with pronounced anti-angiogenic and anti-cancer activity in pre-clinical models; this short sequence comprises only 4% of the PEDF mass and was recently found to induce apoptosis in cultured OvCa cells. Intravitreal P18 also inhibits ocular neovascularization in preclinical AMD models.

We now have invented new technology which greatly improves on P18 by discovering much smaller and more practical active fragments within P18, with modifications allowing them to be linked to nano-device carriers through metastable ester bonds with a capacity to achieve a range of release rates. The size and charge of the carriers allows them to be retained in body tissues, especially in the peritoneum and the eye for prolonged and focused action. The new peptides are made into prodrugs through ester bridging, directly, or through additional, more stable links to carriers. This involves the active amino acid sequences where ester forming di-carboxylic acid appendages retain or increase anti-tumorigenic and anti-angiogenic activity. We also describe methods for esterifying and attaching these to carrier nanoparticles (see below for details). Also described are the methods of analysis to determine the rates of ester breakdown and drug release, enabling choice of the optimal ester form to give the desired half-life for a particular therapeutic indication. Active amino acid sequences, which do not occur naturally have led to unexpectedly more potent peptides with higher net positive charge for prolonged retention in vitreous.

U.S. Pat. No. 8,198,406 disclosed the following sequence otherwise referred to as "P18": Acetyl-Asn-Phe-Gly-Tyr-Asp-Leu-Tyr-Arg-Val-Arg-Ser-Ser-Thr-Ser-Pro-Thr-Thr-Asn-amide (Ac-N-F-G-Y-D-L-Y-R-V-R-S-S-T-S-P-T-T-N-NH$_2$) (SEQ ID NO: 15), with capped or uncapped termini. A peptide this large is potentially immunogenic, expensive to manufacture and difficult to isolate in high purity. It has too many side chains to afford simple linkage chemistry as a prodrug. Thus its therapeutic use would require daily injections at high cost. This could be overcome as a depot in ester prodrug form, thus coupled to alkyl hydroxyl groups on carriers; furthermore, there are already 6 such groups potentially competing on the peptide itself. The one internal Asp carboxyl group is not suited to ester formation, being unstable through internal peptide cyclization.

We have solved these problems by identifying the smaller active sub-region (underlined above) and by chemical modification, adding new carboxyl groups and replacing the internal (Asp) carboxyl with a neutral amino acid. By testing anti-angiogenic activity in assays (blocking endothelial cell migration or induction of apoptosis), we compared shorter fragments with full-size P18 and identified amino acids 3-11 as a fully active, potent core. We then examined the activity of the same peptide appended with di-carboxylic acids as amides to the N-terminus to be used as a practical linkage site, via succinic, glutaric and adipic acids, and also with beta-Alanine added to the C-terminus. We found it necessary to add the N-methyl amino acid, Sarcosine (Sar) for coupling at the N-terminus to insure stability of succinic or glutaric amide half-esters that could cyclize rapidly when attached to ordinary (non-methylated) amino acids.

We discovered, by means of a caspase-3 activation assay, that the optimal small peptides induce apoptosis in ovarian cancer (OvCa) cells in vitro, and that this activity correlates with their potency in blocking the VEGF-stimulated sprouting of capillary tubes from small segments of explanted mouse choroid. This finding predicts activity against wet macular degeneration, retinopathy of prematurity and diabetic retinopathy as well as activity against OvCa and possibly other cancers. Our optimal linkable carboxy-peptide, starting with glutaric-Sar, was unexpectedly found to be 3-5 fold more potent than uncapped or succinyl peptide in these assays. Furthermore internal replacement of negatively charged aspartate by neutral asparagine, when glutarate or adipate is N-terminally appended, improved biologic potency by up to 5-fold. Replacement of the Val-Arg-Ser sequence from within P18 with Pro-ethylamide, Val-Pro-ethylamide or Pro-ethylamide, or Val-Gln-Ser also increased potency while lowering the peptide net charge.

In order to obtain a range of ester prodrugs, we developed syntheses of glutaryl or adipoyl Sar, Gly, or Sar-Gly modified peptides and their esters with amino alcohol linkers, followed by stable attachment of the amino groups of the amino alcohol linkers as amides to carriers having multiple surface carboxyl groups. These include cross-linked hyaluronic acids, and carboxy dendrimers having 16, 32, or 64 carboxyl groups per particle. The amino-alcohol esters can also link as amides to maleic anhydride-based polymers such as Gantrez™, which are approved for intraperitoneal use.

When carrier particles have uncharged surface groups as in polysaccharides like dextran or in hydroxylated dendrimers, amino groups of the amino alcohol linkers can be stably linked to surface hydroxyl groups as carbamates, The peptides can be released from the particles via ester hydrolysis of the ester bond between the carboxy-peptides and the amino alcohol linkers.

Alternatively, for shorter ester hydrolysis half-lives (7-10 days) we include direct esterification of the adipoyl or glutaryl peptides to hydroxyl groups of poly-OH polymers like dextran, after the latter are activated with mesitylene sulfonyl chloride. The peptides described here are potently active 8-10 amino acid fragments of P18 with appended di-carboxyl groups where a free carboxyl group is directly esterified to either (A) hydroxyl groups of polysaccharides (e.g. dextran) with particle sizes ranging from 0.01 to 20 microns in diameter, or (B) bridging amino-alcohols where the amino groups are attached through amide bonds to carboxyl groups of poly-carboxylated polymer carriers such as carboxylated dendrimers (G-1.5-G-4.5, 16-128 carboxyl groups per dendrimer) or nanogels derived from crosslinked hyaluronic acid or from condensed dextrans with diameters ranging from 0.01-20 microns. An important aspect of this construct is that peptide-loaded carriers (e.g., when loaded with SEQ ID NO:4, having a net charge of +2 when esterified) have a positive zeta-potential, i.e. a net positive charge in order to immobilize them at their site of injection through multiple weak ionic interactions. This derives from the fact that each attached peptide, when esterified has a net charge of +1 or +2, and is especially critical for use in the eye, which contains high concentrations of the viscous poly-anionic hyaluronic acid (HA). Thus an ideal particle to be used for intravitreal injection will be less than 200 nm in diameter, a size that does not impede diffusion out of the eye when neutral or negatively charged, but in our system will have net charge of +20 to +100 per particle, for long-term drug release. Ideally, >50% of particles injected in 0.05 ml should be contained at the injection site by adherence to HA in the vitreous humor. The peptide-loaded carrier must be transparent for use in the eye, this is a property of nanogel networks and also of the much smaller dendrimers.

We identified active conjugable peptides, succinate-Sar-P3-11, glutarate-Sar-P3-11, adipate-Sar-P3-11 and adipate-P3-11 also shorter peptides with only 8-9 amino acids, where the distal Arg of these sequences is removed and replaced by neutral amino acids. All identified peptides are at least as active as the parental P18 peptide. Importantly, these peptides are shorter than 12 amino acids, and therefore not likely to be immunogenic. Their production cost and purity will be practical, while the production and purification of larger peptides is difficult and expensive. The amino acid sequence of SEQ ID NO:1 is identical to that found in human PEDF and in P18 and, like P18, has a net charge of +1. SEQ ID NO:1 has the advantage of being small. SEQ ID NOs: 2, 4, 6, 7, 8, 9 have the additional advantage of containing N-terminal carboxylates for ester linkage. SEQ ID NOs:4, 6, 7, 8, 9, 10, 11, 12, 13 also have Asn (N) replacement of Asp (D), restoring the original charge, which surprisingly enhances potency by 2-10 fold. SEQ ID NOs:7, 8, 9, 10, 12 also have replaced the second Arg with other neutral amino acids, leading to a changed net charge of zero and 6-10 fold increased potency. These new amino acid sequences are not known to exist in nature, containing 3-4 amino acids (Sar, Asn, Pro, Gln) not found in this 9 amino acid segment of human PEDF or in any known protein.

For use in the eye, the ideal half-life of ester cleavage by simple hydrolysis at 37° C. and pH7.4 should be 10-100 days, 20-60 days being ideal. Approximately 1 mg of peptide attached to 0.1-1 mg of the carrier would be delivered in the eye in 50p injection volume.

For simplified testing of release rate, amino alkyl or amino aralkyl esters of various amino alcohols are made with adipoyl or glutaryl-Sar-Gly-amido rhodamine. These are attached to a carrier with >10,000 MW overall molecular weight with total Absorbance at 550 nm measured after dialysis. Ester linkage to carrier may be direct or via amino alcohol bridge. Examination of Absorbance at 550 nm released into filtrate of spin filtration (10 kDa cutoff) at various days after incubation gives the rate of ester breakdown in buffer. This is repeated in the presence of animal vitreous humor or ascites fluid from mice with orthotopic ovarian cancer to confirm release rates. For IP delivery to treat OvCa or endometriosis 20-400 mg of carrier linked-peptide can be delivered in 1-25 ml of injection fluid (buffer or saline). Sterilization will be most facile where loaded particles are <200 nm diameter. Larger carriers may require gamma-ray sterilization. Ideal IP release rates for peptide should be in a similar range.

REFERENCES

Kyoungmin Park, Ji Jin, Yang Hu, Kevin Zhou, Jian-xing Ma, "Overexpression of Pigment Epithelium-Derived Factor Inhibits Retinal Inflammation and Neovascularization," Am. J. Pathol 178(2): 688-698; 2011.

Payam Zahedi, James Stewart, Raquel De Souza, Micheline Piquette-Miller, Christine Allen, "An injectable depot system for sustained intraperitoneal chemotherapy of ovarian cancer results in favorable drug distribution at the whole body, peritoneal and intratumoral levels," Journal of Controlled Release, Volume 158, Issue 3, 28 Mar. 2012, Pages 379-385.

Barber E L, Zsiros E, Lurain J R, Rademaker A, Schink J C, Neubauer N L, "The combination of intravenous bevacizumab and metronomic oral cyclophosphamide is an effective regimen for platinum-resistant recurrent ovarian cancer," J Gynecol Oncol. 2013 July;24(3):258-64.

Filleur S, Volz K, Nelius T, Mirochnik Y, Huang H, Zaichuk T A, Becerra S P, Yap R, Veliceasa D, Shroff E H, Volpert O V, "Two functional epitopes of pigment epithelial-derived factor block angiogenesis and induce differentiation in prostate cancer," Cancer Res. 2005; 65:5144-52.

Mirochnik Y, Aurora A, Schulze-Hoepfner F T, Deabes A, Shifrin V, Beckmann R, Polsky C, Volpert O V, "Short pigment epithelial-derived factor-derived peptide inhibits angiogenesis and tumor growth," Clin Cancer Res. 2009; 15(5):1655-63.

Xu Q, Boylan N J, Suk J S, Wang Y Y, Nance E A, Yang J C, McDonnell P J, Cone R A, Duh E J, Hanes J, "Nanoparticle diffusion in, and microrheology of, the bovine vitreous ex vivo," J Control Release. 2013 Apr. 10;167(1):76-84.

U.S. Pat. No. 8,530,416.
U.S. Pat. No. 8,278,284.
U.S. Pat. No. 8,198,406.
European Patent Publication No. 1265627.

Example 2—Small Peptides for the Treatment of Neovascular Disease, Inflammatory Disease and Cancer We have discovered biologically active peptide sequences within PEDF including the 18-amino acids long P18. Novel modified peptides and new peptide sequences disclosed herein are exemplified by SEQ ID NOs:1-13. SEQ ID NO:1 is an active truncation of P18 (see U.S. Pat. No. 8,198,406) having only 9 amino acids (i.e., ½ of amino acids in P18). FIG. 1 provides $ED_{50}$ (50% effective dose) values for the peptides wherein $ED_{50}$ is the measure of anti-angiogenic potency obtained by quantitative assessment of apoptosis of activated human endothelial cells (EC) as described in FIG. 3. SEQ ID NOs:2-11 are modifications of the native PEDF sequence, which improve potency ($ED_{50}$) by 2-20 fold and enable formation of prodrugs. In preferred embodiments internal charged residues are removed or replaced by neutral amino acids, and N-terminal replacement or addition of sarcosine is utilized to stabilize glutaric and adipic ester prodrugs. Replacement of anionic aspartate by neutral asparagine in SEQ ID NOs:4-13 leads to improved potency, which is further enhanced by N-terminal addition of dicarboxylic acids (glutaric, adipic, suberic), as illustrated in the more potent anti-tumor activity of SEQ ID NO:4, compared with SEQ ID NO:2 seen in FIG. 5A. Truncations and specific amino acid changes at the C-terminus also enhance potency ($ED_{50}$), as exemplified in SEQ ID NO:10.

FIG. 2 shows that the described peptides reduce cell viability in multiple human and mouse ovarian cancer cells, while normal ovarian epithelial cells (nOSE) and non-stimulated epithelial cells (EC) remain viable. As illustrated by the results of FIG. 2, ovarian cancer cells, normal ovarian epithelial cells (nOSE), and unstimulated mouse endothelial cells (mEC) were treated with increasing concentrations of SEQ ID NO:2 and viability was measured using a WST assay. The differences observed at 10 and 100 nM are statistically significant P<0.02, as determined by Wilcoxon log rank test (Graph Pad Prizm software).

Figure 3:
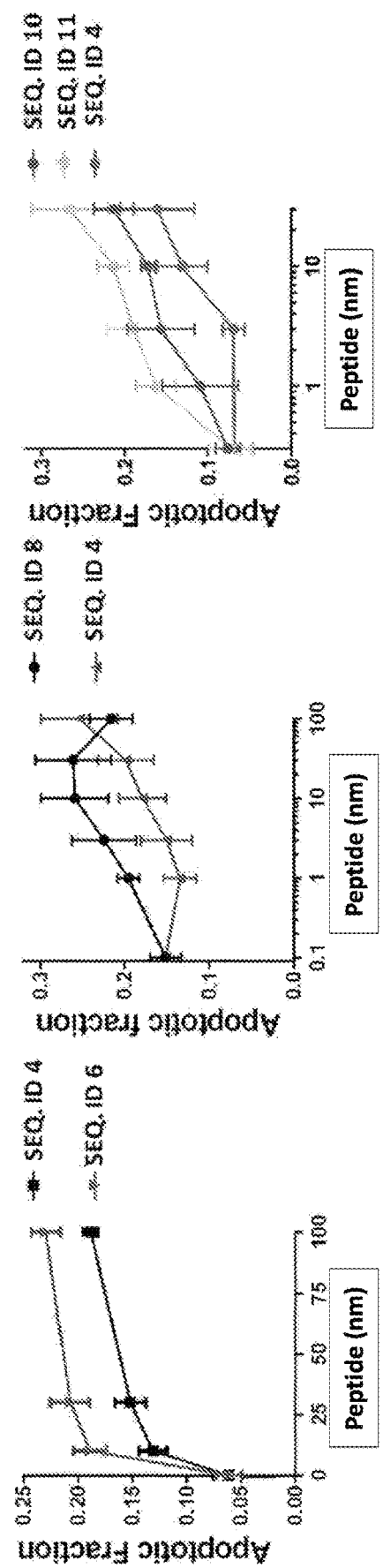
FIG. 3. Relative potency of peptides at inducing endothelial cell (EC) apoptosis. Human microvascular EC (HMVEC) were seeded on glass coverslips and grown in EGM, supplemented with defined growth factors and full serum (5%) to 80-90% confluence. The cells were transferred overnight in the medium with 1% serum, w/o growth factors. VEGF (10 ng/ml) was added to induce pro-angiogenic function/survival. Peptides were added at indicated concentrations. After 48 h the cells were fixed in 1% buffered paraformaldehyde and apoptosis detected by in situ TUNEL. Apoptotic cells were quantified in ~10 10× fields per condition and apoptotic fraction (apoptotic/total cells) calculated for each condition. Apoptosis induced in endothelial cells by indicated peptides (SEQ ID NO:6, 8, 10, and 11) is compared to SEQ ID NO:4.

FIG. 3 illustrates the biological activity of various peptides at inducing apoptosis in endothelial cells at various concentrations. The modified peptides of SEQ ID NOs:6,8, 10, and 11 were compared to the modified peptide of SEQ ID NO:4 at the indicated concentrations.

Figure 4:
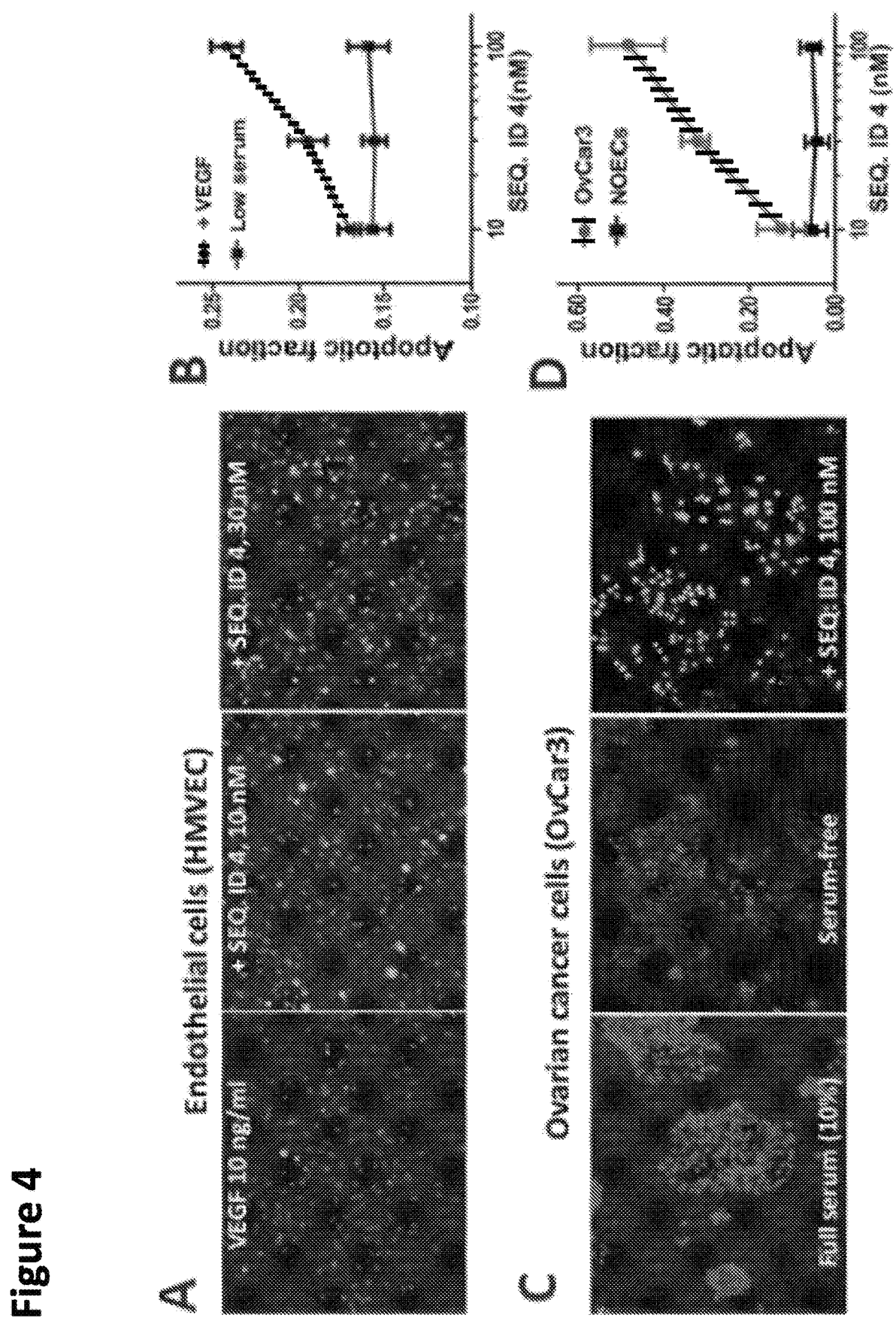
FIG. 4. Selective cytotoxic activity of SEQ. ID NO:4 in proliferating endothelium and cancer cells. EC apoptosis was measured as in FIG. 3. Panel (A) Representative images of ECs treated with SEQ ID NO:4. VEGF is present in all conditions and apoptosis is assessed by TUNEL (fluorescence) and all cells are labeled with DAPI (nuclear marker). Panel (B) Specific pro-apoptotic activity of SEQ ID NO:4 in VEGF-stimulated endothelial cells but not in quiescent endothelium (low serum). Panel (C) Specific proapoptitc activity in ovarian cancer cells in serum-free media with and without SEQ ID NO:4. Cells in full serum (10%) are shown for comparison. Panel (D) Specific proapoptitc activity in ovarian cancer cells (OvCar3) but not in normal ovarian epithelial cells (NOECs) induced by SEQ ID NO:4. Ovarian cancer cells and normal ovarian epithelial cells were grown to 70% confluence, transferred in serum-free medium and treated with indicated peptide concentrations for 48 hrs.

FIG. 4 provides further experimental results illustrating the biological activities of the disclosed peptides. In FIG. 4, the peptides' activities were measured using apoptosis of VEGF-stimulated endothelial cells as the measured property. The results confirm the selectivity of peptides' effects on both of activated (angiogenic) ECs (FIG. 4, Panel (B)) and on ovarian cancer cells (FIG. 4, Panel (D)) using apoptosis as measure of activity.

Figure 5:
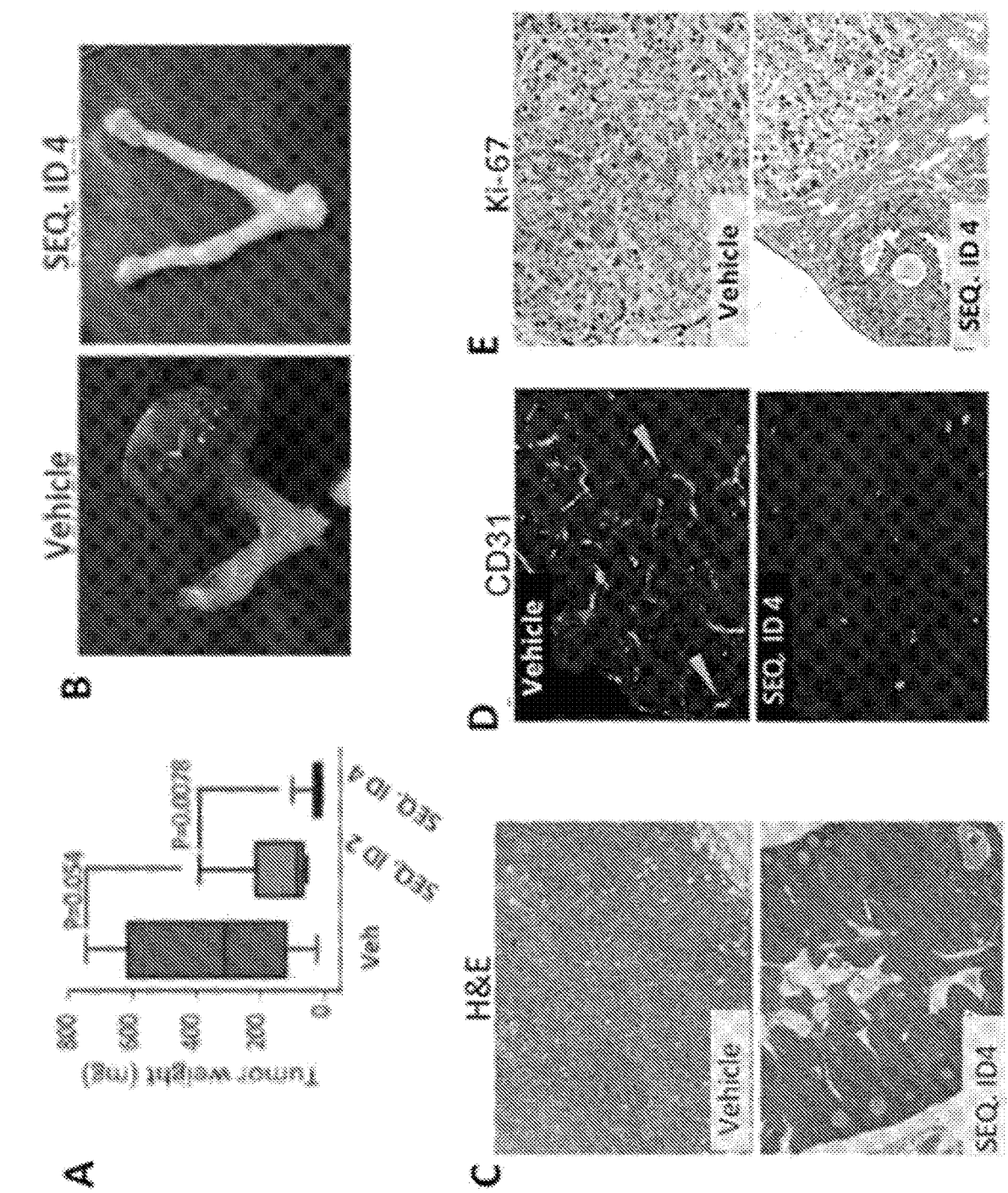
FIG. 5. PEDF peptides inhibit the growth of orthotopic ovarian tumors. Mice were implanted with $10^6$ ovarian cancer cells in the left ovary and tumors allowed to reach progressive growth phase. The mice were treated with continuous peptide administration (5 mg/kg) for 4 weeks. At the end of treatment, mice were euthanized, the tumors extracted and processed for analyses. Tumor growth quantitation was accomplished in real time by the cells expressing a bioluminescent probe. Panel (A) Average tumors weights at the time of sacrifice. Panel (A) shows the greater efficacy in vivo of SEQ ID NO:4 compared to SEQ ID NO:2, consistent with their in vitro potencies. Panel (B) Representative tumor images form control group and the group treated with SEQ ID NO:4. Panel B shows a representative difference in tumor size at endpoint. Panel (C) Representative histology in control and treated groups. Panel (C) shows normal ovarian morphology in the ovaries of mice treated with SEQ ID NO:4. Panel (D, E) SEQ ID NO:4 blocks tumor angiogenesis and cancer cell division in vivo. Ovarian tumors from mice treated with SEQ ID NO:4 or control vehicle were stained for the marker of blood vessels (CD31) or proliferation marker (Ki-67). Note visible decreases in the number of tumor blood vessels (Panel (D)) and cell proliferation (Panel (E)) in the presence of SEQ ID NO:4, compared to vehicle control.

FIG. 5 shows the capacity of SEQ ID NO:2 and SEQ ID NO:4 to cause shrinkage in a mouse of human OVCAR3 tumors growing in the peritoneal space. Mice were implanted with $10^6$ ovarian cancer cells in the left ovary and tumors were allowed to reach progressive growth phase. The mice then were treated with continuous peptide administration (SEQ ID NO:4, 5 mg/kg) for 4 weeks. At the end of treatment, mice were euthanized, the tumors extracted and processed for analyses. Tumor mass was measured at the endpoint (Panel (A)). Representative tumors are shown in panel (B) and histopathology of tumors is presented in panel (C). Ovarian tumors from mice treated with SEQ ID NO:4 or control vehicle were stained for the marker of blood vessels (CD31) or proliferation marker (Ki-67). We observed a visible decrease in the number of tumor blood vessels (FIG. 5, Panel (D)) and cell proliferation (FIG. 5, Panel (E)) in the presence of SEQ ID NO:4, compared to vehicle control. In FIG. 5, panels (A-C) and B show reduced tumor mass and normalized histology in the presence of SEQ ID NO:4; these effects are consistent with the apoptotic effects of SEQ ID NO:4 on both activated EC and OVCAR3 observed in vitro.

Figure 6:
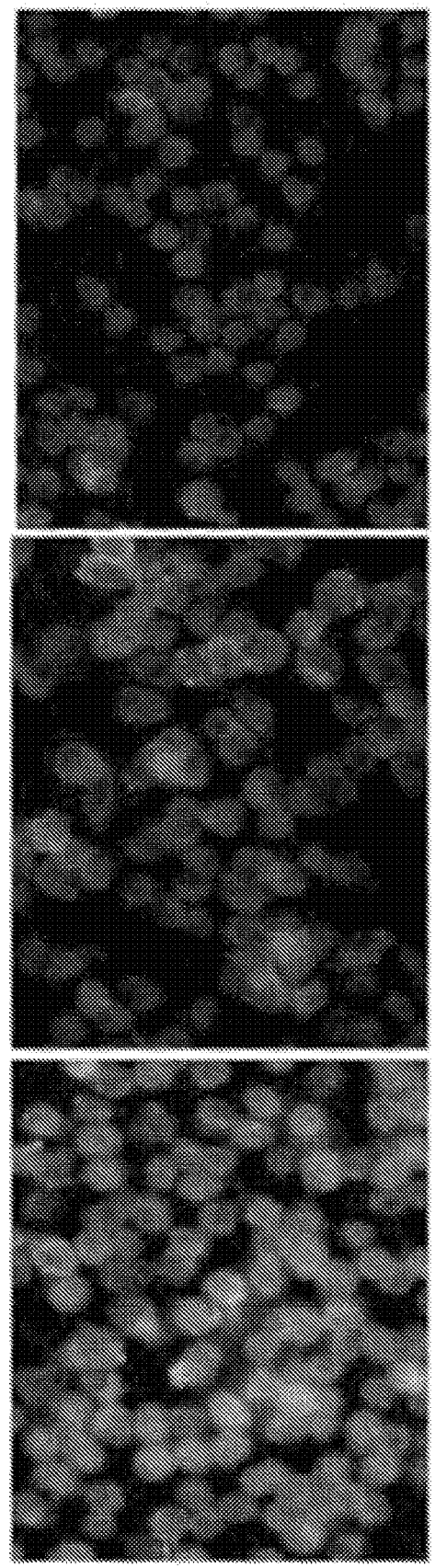
FIG. 6. SEQ ID NO:4 enables mouse macrophages to kill tumor cells and reduces their immunosuppressive activity. Panels (A, B). Normal ovarian epithelial cells (NOE) and ovarian cancer cells (Ovcar-3) were cultured alone or admixed with macrophages (Raw264.7) at 1:3 ratio. All cells were treated with SEQ ID NO:4 (10 nM) and cell death visualized (Panel (A)) and quantified (Panel B)) using TUNEL stain (green). Panel (C) Tumor cell killing was due to a macrophage-derived death molecule called TRAIL (expression induced by SEQ ID NO:4). This was demonstrated by adding TRAIL inhibitor (decoy receptor-1 (DcR-1)) to the co-culture of ovarian cancer cells and macrophages and measuring cell death (Apoptosis) as in Panel (A). Panel (D) illustrates that SEQ ID NO:4 attenuates immunosuppressive properties of tumor-associated macrophages. In ovarian cancer, macrophages are a rich source of immunosuppressive molecule PD-L1, which interferes with ovarian cancer cells recognition by T lymphocytes. Note that SEQ ID NO:4 reduces the expression of PD-L1 by macrophages. Cell nuclei are highlighted.

FIG. 6 shows the immunostimulatory effects of the SEQ ID NO:4 peptide in macrophages which may be responsible for the anti-cancer activity of SEQ ID NO:4. In FIG. 6, Panels (A, B), normal ovarian epithelial cells (NOE) and ovarian cancer cells (Ovcar-3) were cultured alone or admixed with macrophages (Raw264.7) at a 1:3 ratio. All cells were treated with SEQ ID NO:4 (10 nM) and cell death was visualized (Panel (A)) and quantified (Panel B)) using TUNEL stain. Panel (C) illustrates that tumor cell killing was due to a macrophage-derived death molecule called TRAIL which was induced by SEQ ID NO:4. This was demonstrated by adding TRAIL inhibitor (DcR-1, decoy receptor-1) to the co-culture of ovarian cancer cells and macrophages and measuring cell death (Apoptosis) as in Panel (A). In ovarian cancer, macrophages are a rich source of immunosuppressive molecule PD-L1, which interferes with ovarian cancer cells recognition by T lymphocytes. Panel (D) illustrates that SEQ ID NO:4 attenuates immunosuppressive properties of tumor-associated macrophages by inhibiting the production of PD-L1.

Figure 7:
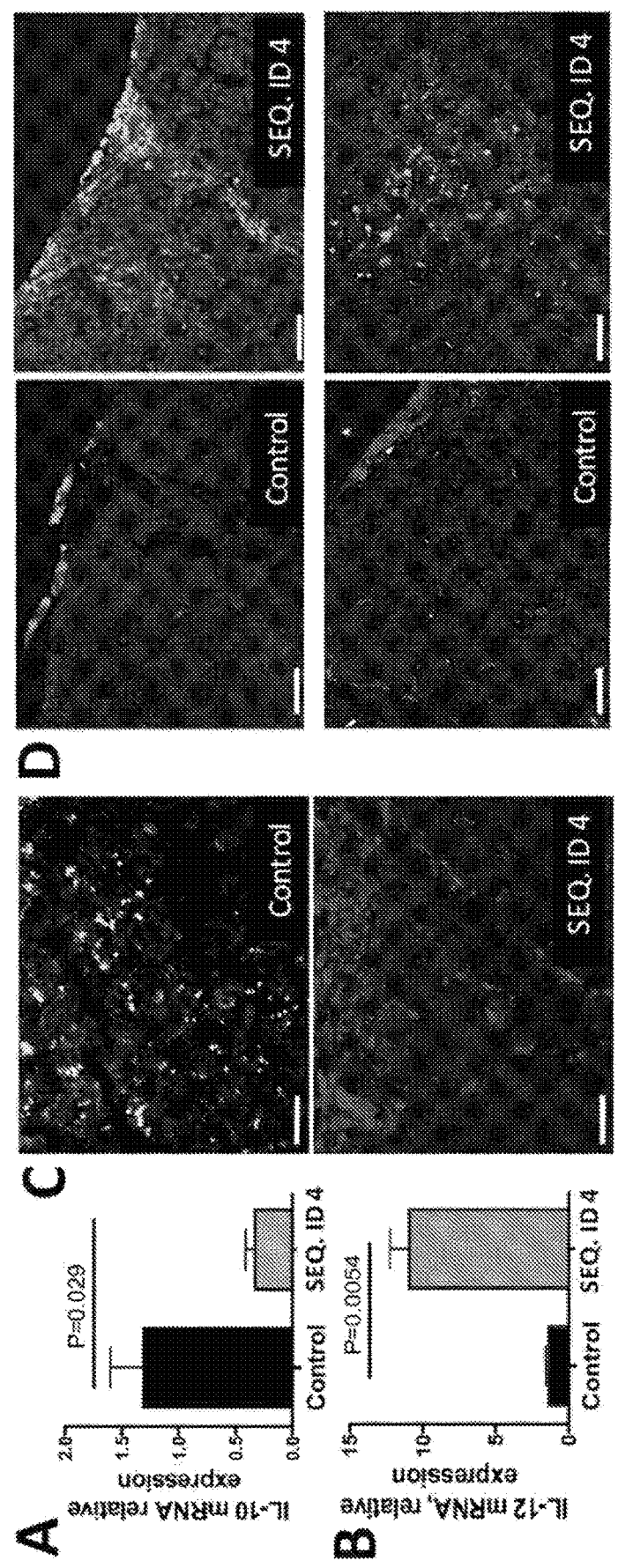
FIG. 7. SEQ ID NO:4 promotes tumor-suppressive macrophages in vivo. This is illustrated in Panel (A) by decreased expression of mRNA for the marker of tumor-promoting macrophages (IL-10) and in Panel (B) by increased expression of an mRNA encoding the marker for the tumor-suppressive phenotype (IL-12) in the macrophages cultured in the presence of SEQ ID NO:4. Panel (C). Treatment with SEQ ID NO:4 eliminates the tumor-promoting macrophages (top), while tumor suppressive macrophages are prominent (bottom). Panel (D) illustrated that treatment with SEQ ID NO:4 also increases macrophage infiltration into tumors. Panel (E) illustrates that, in tumors treated with SEQ ID NO:4, macrophages acquire the ability to kill tumor cells in their proximity.

FIG. 7 shows that SEQ ID NO:4 changes the subtype of macrophages to a tumor-suppressive subtype and stimulates the infiltration of the tumor-suppressive macrophages into the ovarian tumors, which is associated with increased ovarian cancer cell killing. Panel (A) illustrates decreased expression of mRNA for the marker of tumor-promoting macrophages (IL-10), and Panel (B) illustrates increased mRNA levels of a marker for the tumor-suppressive phenotype (IL-12) in the macrophages cultured in the presence of SEQ ID NO:4. Panel (C) illustrates that treatment with SEQ ID NO:4 eliminates the tumor-promoting macrophages (top, control treatment), while tumor suppressive macrophages are prominent (bottom, treatment with SEQ ID NO:4). Panel (D) illustrates that treatment with SEQ ID NO:4 also increases macrophage infiltration into tumors. Panel (E) illustrates that, in tumors treated with SEQ ID NO:4, macrophages acquire the ability to kill tumor cells in their proximity.

Figure 8:
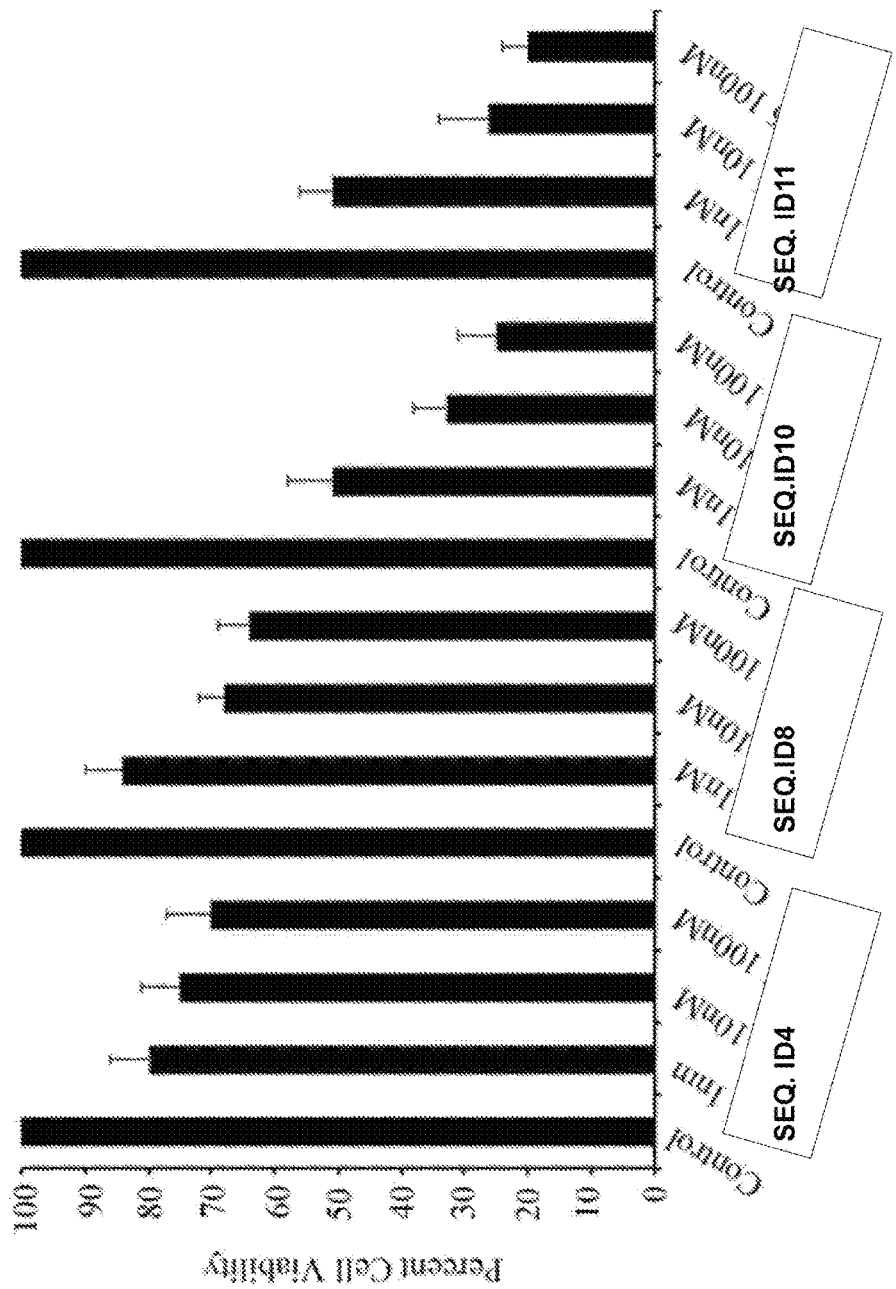
FIG. 8. PEDF peptides decrease viability of osteosarcoma cells. D17 canine osteosarcoma cells were cultured under normal growth conditions and treated with the indicated peptides/concentrations for 24 hours. Cell viability was measured by WST-1 assay. Consistent with their relative potency in other cell killing assays (see above), SEQ. ID NO:10 and Seq. ID NO:11 show higher potency than SEQ. ID NO:4 and SEQ. ID NO: 8. This also shows that both canine cancer cells and human cancer cells are killed by modified PEDF peptides in FIG. 1.

FIG. 8 shows the efficacy of described peptides in decreasing viability of canine osteosarcoma cells, by WST assay. Thus in addition to killing ovarian cancer cells in vitro, as described in FIG. 2, concentrations of the tested peptides between 10 nM and 100 nM, also led to killing of osteosarcoma cells. This shows broad anti-cancer activity of the peptides, potency consistent with that of their causing apoptosis of EC. As with the latter, SEQ ID NO:10 and SEQ ID NO:11 show higher potency than SEQ ID NO:4 and SEQ ID NO:8 in lowering the viability of osteosarcoma cells. These results suggest that the disclosed peptides may be utilized in veterinary applications, for example, in treating canine cancer.

Figure 9:
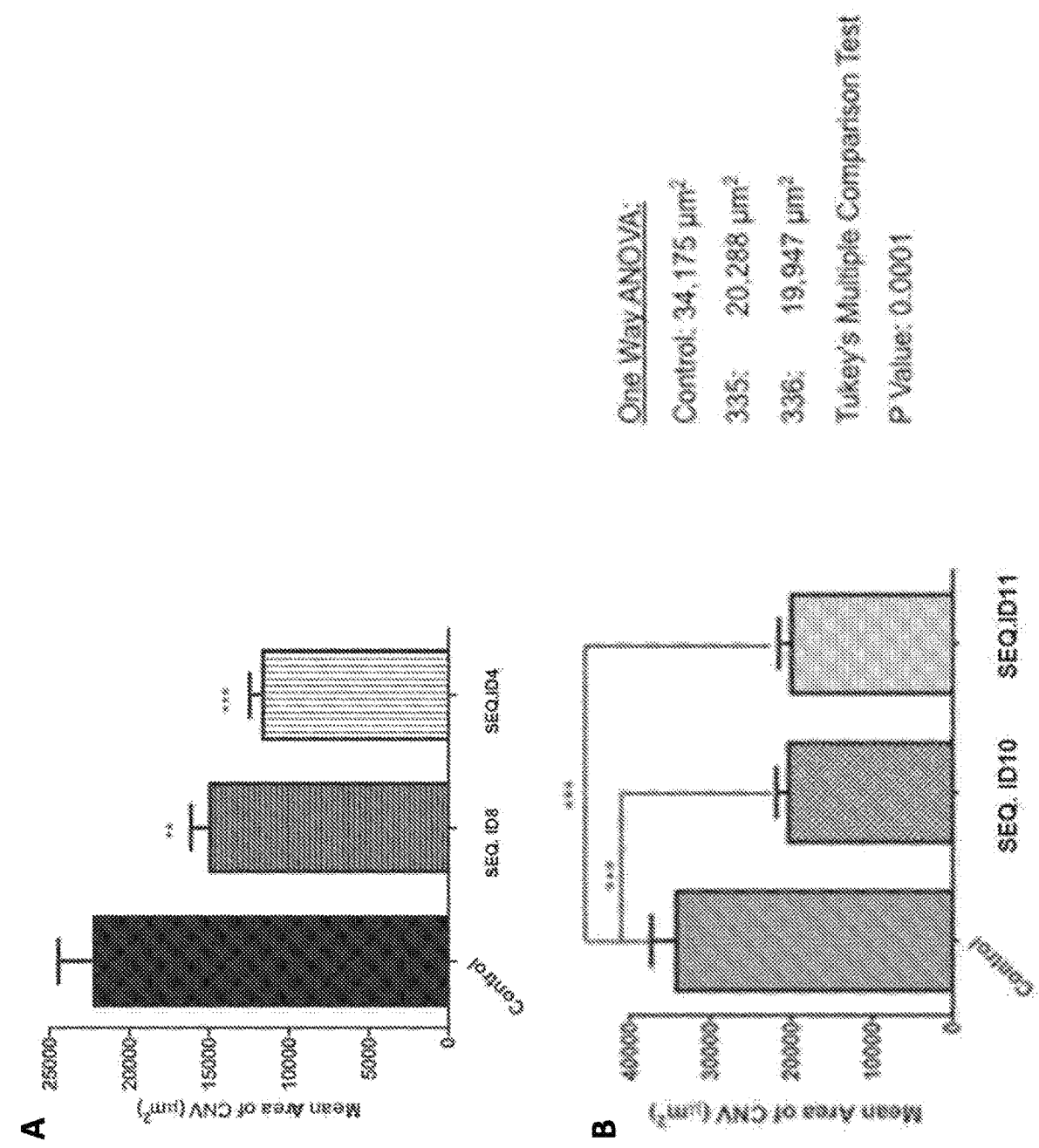
FIG. 9. Peptide inhibition of laser-induced choroidal neovascularization (CNV). Mice were anesthetized for eye injections and were injected intravitreally with 1 µl PBS vehicle control or with 1 µl of 4 mg/ml peptide solution. After 2 days the same mice were re-anesthetized and 3 local retinal laser burns introduced in each eye to induce choroidal neovascularization (CNV). At 14 days post induction, CNV was measured on choroidal-scleral flat mounts using fluorescent antibody stain for ICAM2. PECAM-1 positive CNV area was digitally measured to quantify treatment responses. Panel (A), control, SEQ ID NO:8 and SEQ ID NO:4. Panel (B), control, SEQ ID NO:10 and SEQ ID NO:11.

FIG. 9 shows efficacy of SEQ ID NO:4, SEQ ID NO:10, and SEQ ID NO:11 peptides in mitigating laser induced CNV, an accepted mouse model of exudative ("wet") macular degeneration. Anesthetized mouse eyes were injected intravitreally with 1 µl PBS vehicle control or with 1 µl of peptide solution (4 mg/ml). After 2 days the same mice were re-anesthetized and 3 laser burns introduced onto the retina in each eye to induce choroidal neovascularization (CNV). At 14 days post CNV induction, sacrifice CNV areas were measured on choroidal-scleral flat mounts stained with fluorescent antibody against PECAM-1. The results in FIG. 8 illustrate that the peptides protect against neovascular retinal damage for two weeks when 1 µl of 2-4 mM peptide is injected into mouse vitreous two days prior to laser induction. This result implies the usefulness of the peptides in the treatment of neovascular eye disease.

Figure 10:
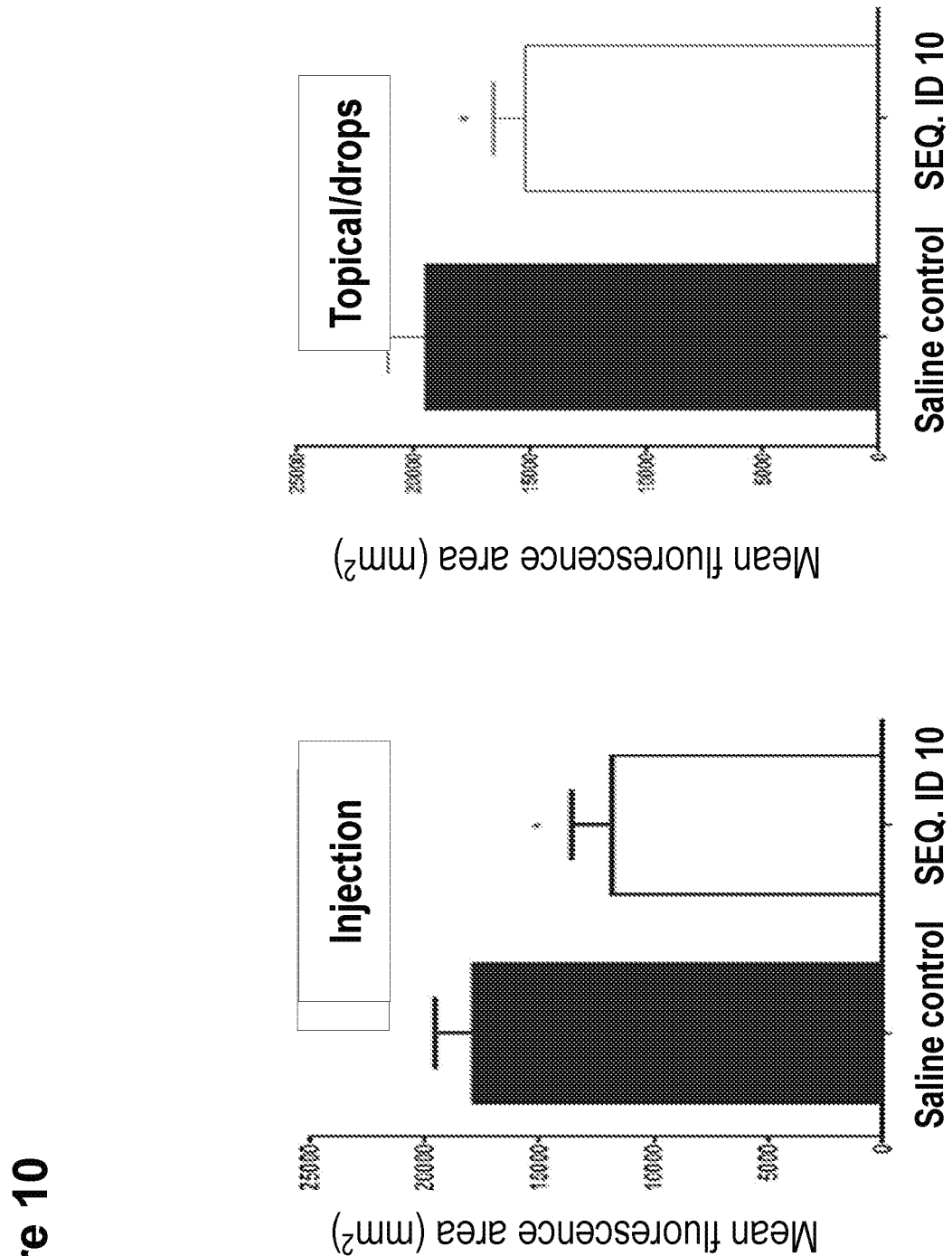
FIG. 10. SEQ ID NO:10 mitigates laser-induced CNV, when administered either by intra-ocular injection, or as eye drops. SEQ. ID NO:10 (4 mg/ml) or saline were injected 3 days prior to CNV induction. In a parallel group, mice were treated twice daily with eye drops containing SEQ. ID NO:10 (10 mg/ml) 7 days prior to CNV induction. After laser induction, eye were continued for 11 days, with final analysis at day 14 post induction. Both delivery methods significantly decreased CNV.

FIG. 10 shows that for peptide SEQ. ID NO 10, having only 8 amino acids and zero net charge at neutral pH, mitigation of laser-induced CNV can be achieved by its administration as eye drops as well as by its injection into the vitreous. Twice daily eye drops (5 ul, 10 mM peptide in saline) begun 7 days before laser induction, then continued over 10 of the ensuing 14 days, significantly reduced CNV compared to controls receiving saline eye drops. This demonstrated efficacy against ocular neovascular disease via eye drop administration.

Figure 11:
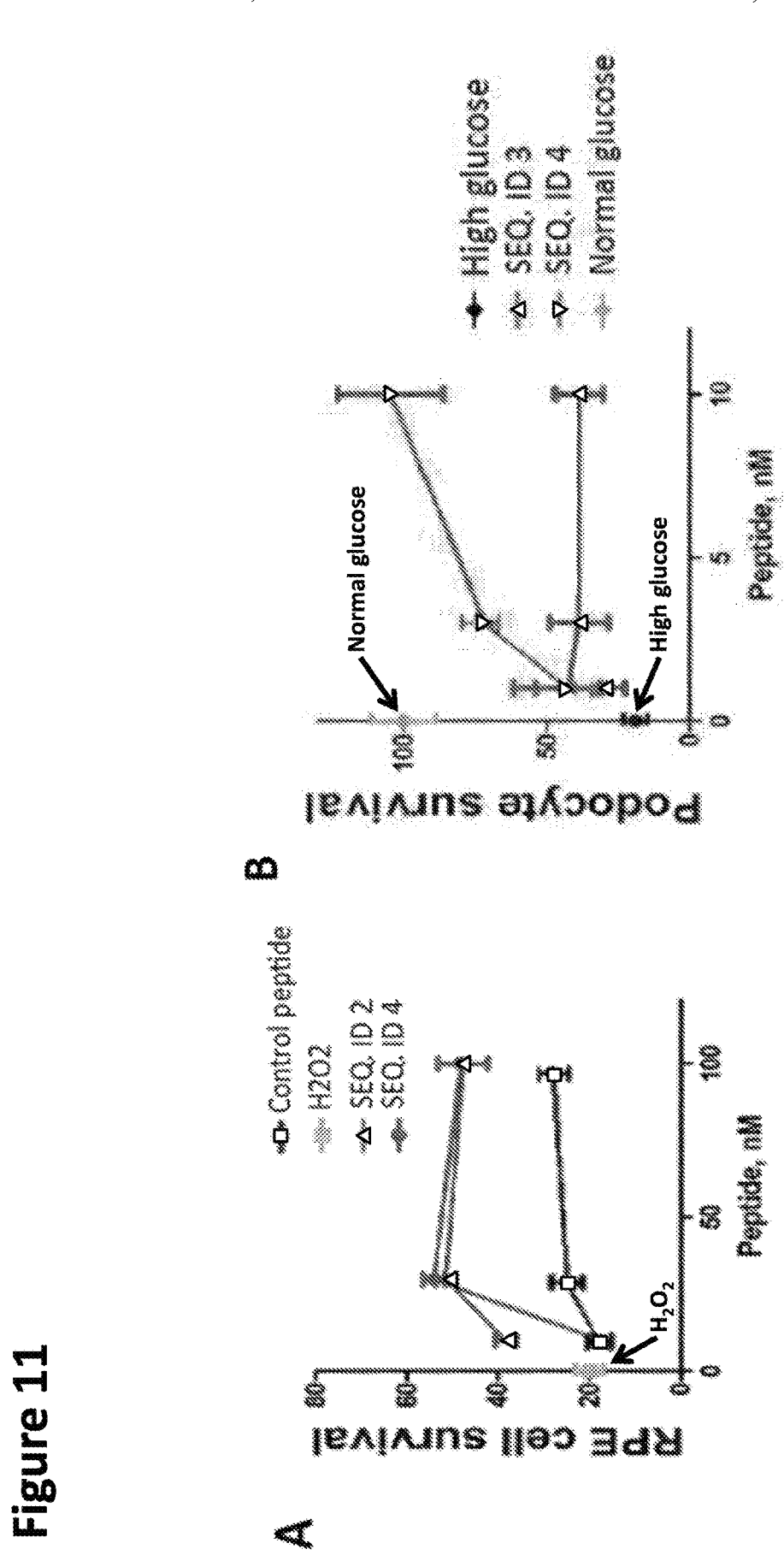
FIG. 11. PEDF peptides protect retinal and renal cells from environmental insults. Panel (A) Protection of retinal pigment epithelial cells (RPE-1) against peroxide-induced toxicity. Panel (B) Protective effects in renal cells (podocytes) from toxic effects of hyperglycemic stress. High glucose (20 mM) and normal (5 mM) glucose conditions are shown for comparison.

FIG. 11 shows that in normal cells peptides show protective activity against cellular stressors. Panel (A) illustrates that the peptides protect renal cells (podocytes) from toxic effects of hyperglycemic stress. High glucose (20 mM and normal (5 mM) glucose conditions are shown for comparison. Panel (B) illustrates that the peptides protect retinal pigment epithelial cells (ARPE-1) against peroxide-induced toxicity. In particular, Panel (A) shows that SEQ ID NO:2 and SEQ ID NO:4 make retinal pigment epithelial (RPE) cells less susceptible to hydrogen peroxide, a reactive oxygen species (ROS) produced during inflammation, as seen in dry macular degeneration. In Patent (B), kidney cells (podocytes) in vitro are sensitive to toxicity by high glucose concentration, which is mediated by endogenous production of ROS (see FIG. 11 below). SEQ ID NO:4, at 10 nM, fully protects the kidney cells from death implying that SEQ ID NO:4 is useful in protecting kidney damage in diabetes.

Figure 12:
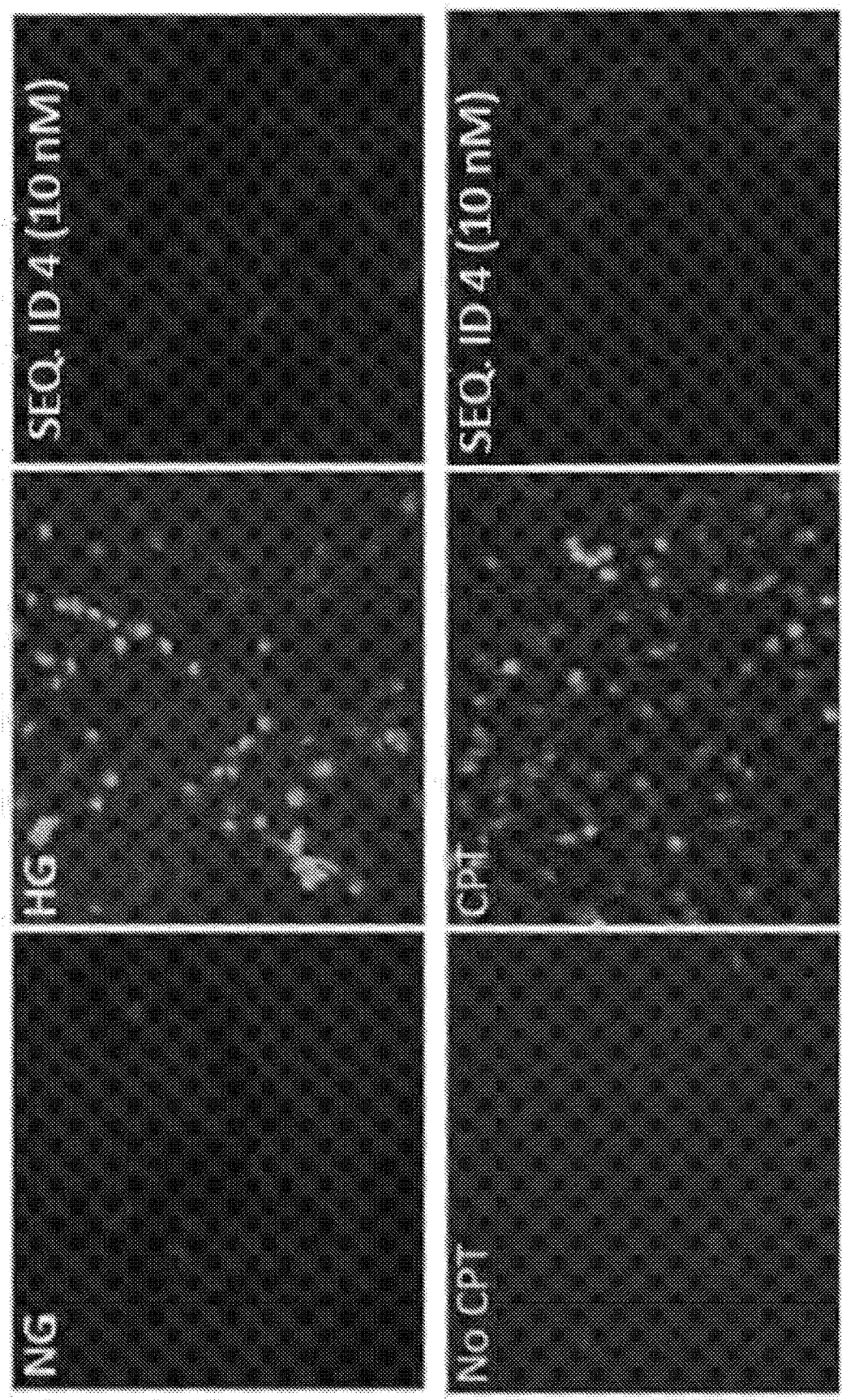
FIG. 12. SEQ ID NO:4 inhibits production of toxic reactive oxygen species (ROS). ROS were visualized using green fluorescent stain. Top row: ROS production in renal cells (podocytes) from in normal (NG, 5 mM) and high glucose (20 mM, HG) conditions are shown for comparison and SEQ ID NO:4 added to high glucose condition. Bottom row: ROS production by podocytes treated with chemotherapy agent, cisplatin (CPT) in the presence and absence of SEQ ID NO:4 peptide.

FIG. 12 examines production of toxic ROS in kidney podocytes in vitro, by their exposure to high glucose, and to the chemotherapeutic agent, cisplatin, for which podocyte damage is a dose-limiting toxicity in the kidney. FIG. 10 illustrates that ROS production was stimulated by hyperglycemia (HG) or cisplatin (CPT) as "stressors." Reactive oxygen species were detected using peroxide-specific stain by fluorescence. FIG. 10 also illustrates that SEQ ID NO:4 dramatically alleviates ROS production induced by both stressors. This implies the usefulness of SEQ ID NO:4 in protective therapy against kidney damage both in diabetes, and during chemotherapy.

Figure 13:
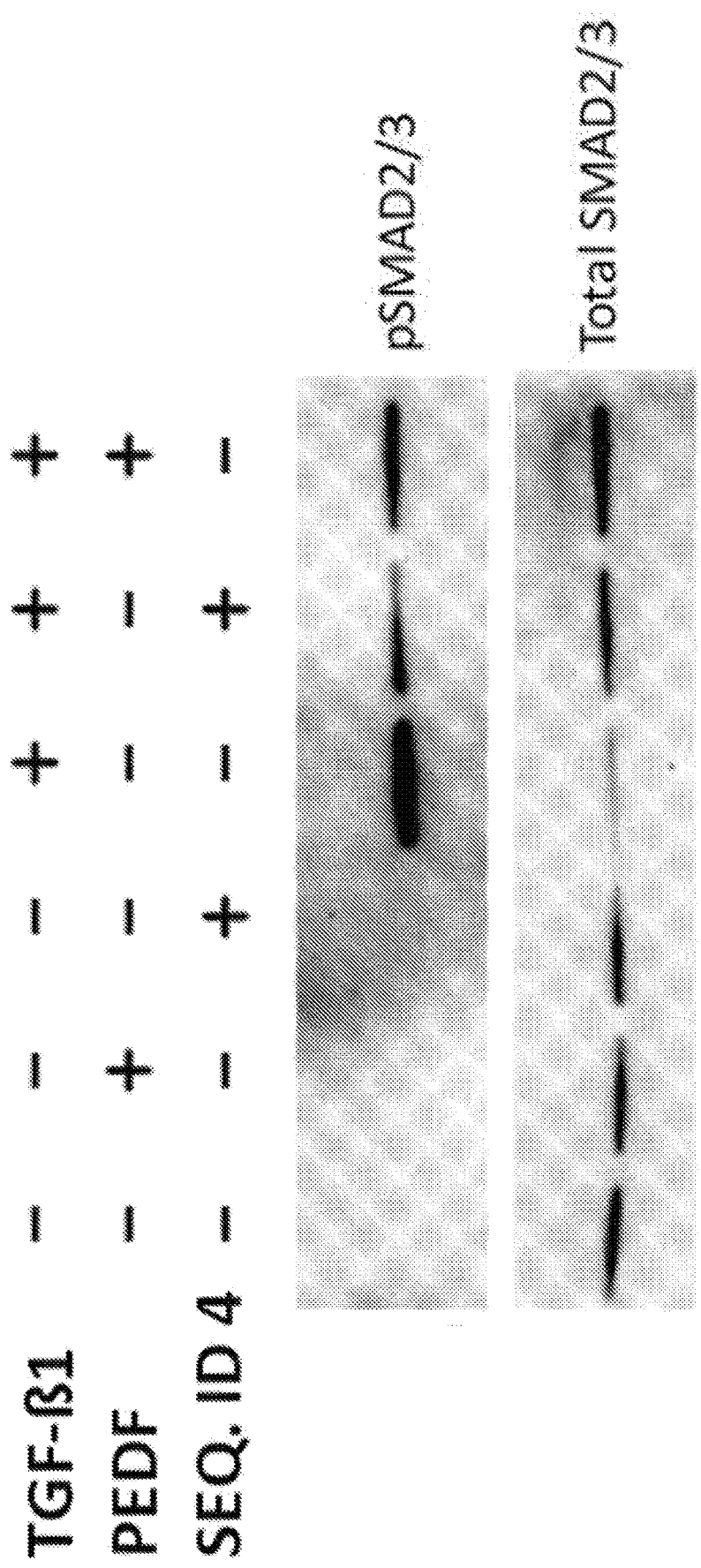
FIG. 13. SEQ ID NO:4 inhibits fibroblast activation. Human primary dermal fibroblasts were activated with TGF-B1 (10 ng/ml), SEQ ID NO:4 (30 nM) was added where indicated and PEDF (20 nM) was used as control. After 24 h the cells were lysed and activation assessed as phosphorylation of pSMAD. Note ~ 5-fold decrease in pSMAD by SEQ ID NO:4.

FIG. 13 demonstrates that pro-fibrotic signaling in fibroblasts (induced by TGF-b1) is suppressed by SEQ ID NO:4. Human primary dermal fibroblasts were activated with TGF-B1 (10 ng/ml), and SEQ ID NO:4 (30 nM) was added where indicated or PEDF (20 nM) was used as control. After 24 h the cells were lysed and pro-fibrotic signaling was assessed by measuring phosphorylation of TGB-β1 target, SMAD2/3. These results have potential implications for the treatment of fibrotic diseases, such as idiopathic pulmonary fibrosis or renal fibrosis due to diabetes or other injury.

Figure 14:
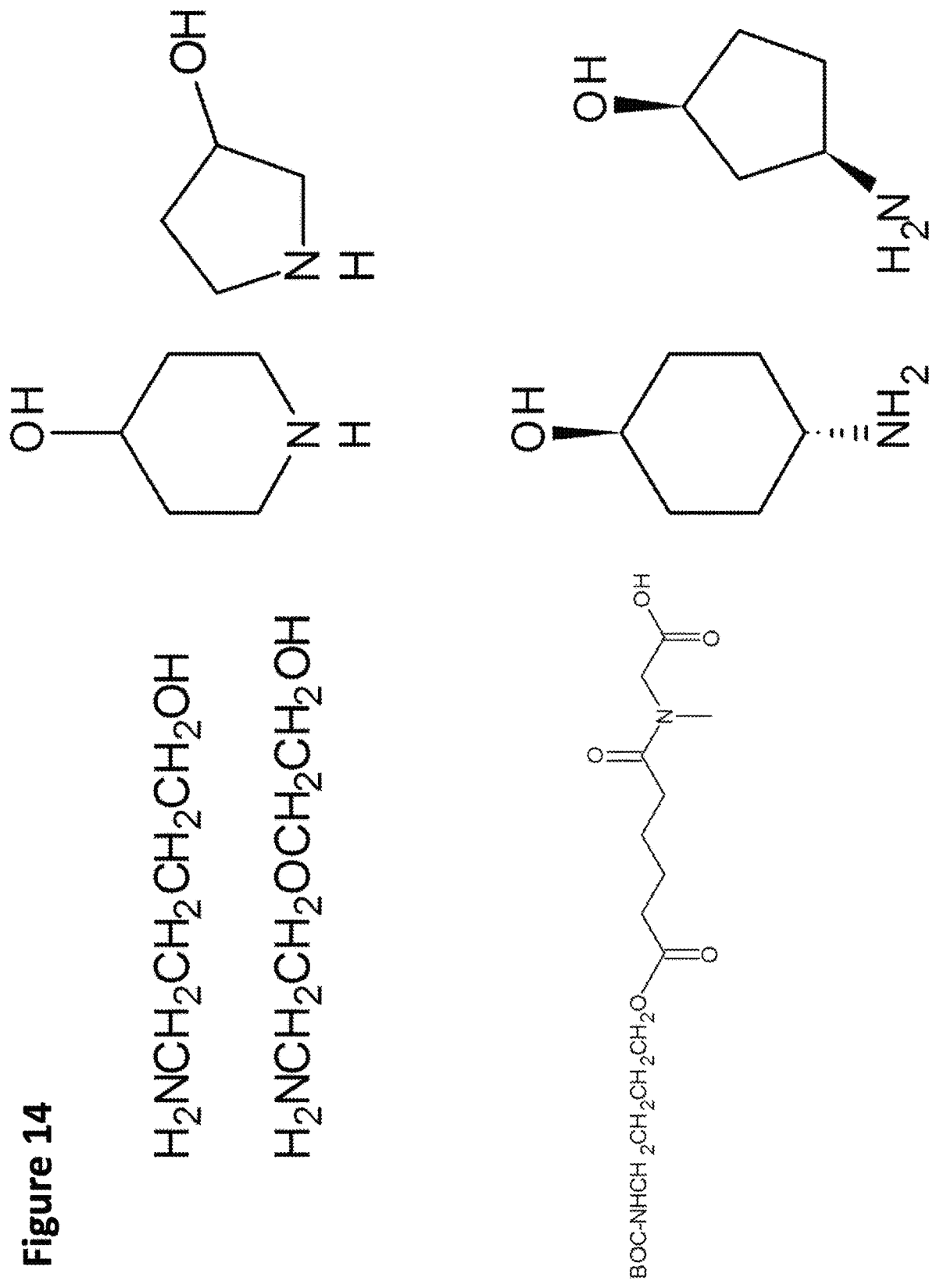
FIG. 14. Amino alcohol ester-bridging groups.

FIG. 14 gives examples of bridging amino-alcohols which, in their amino-blocked forms (eg: N-BOC or N-FMOC amido-alcohols) can be mono-esterified to dicarboxylic acids (glutaric acid, adipic acid), which are then amide linked to the N-termini of peptides shown in FIG. 1, during their solid-state synthesis. After de-blocking, release from resin, and HPLC peptide purification the amino groups are then used to form carbamate or amide linkages to carrier particles. As indicated, in order to obtain a wide range of ester prodrugs, we developed syntheses of glutaryl or adipoyl Sar, Gly, or Sar-Gly modified peptides and their esters with amino alcohol linkers, followed by stable attachment of the amino groups of the amino alcohol linkers as amides to carriers having multiple surface carboxyl groups. These include cross-linked hyaluronic acids, and carboxy dendrimers having 16, 32, or 64 carboxyl groups per particle. The amino-alcohol esters can also link as amides to maleic anhydride-based polymers such as Gantrez™, which are approved for intraperitoneal use. FIG. 14 shows examples of amino alcohols (Z groups) utilized to bridge peptide esters to a carrier, and a blocked carbamato-ester of adipoyl sarcosine for N-terminal capping of a peptide during solid state synthesis. This capping can be applied to the bridging groups shown to prepare dicarboxy-peptide esters ready for linkage to carriers. In FIG. 14, FMOC or t-BOC protected carbamates of the above amino alcohols are esterified to dicarboxylic acid amides of glycine or sarcosine. These carbamates then are appended to the N-termini of growing resin-bound peptide chains on resin during solid state synthesis. Removal of the proximal protecting groups then allows new carbamate or amide attachments to be made to carrier polymers displaying hydroxyl or carboxyl groups on their surface such as dextran or hyaluronic acid.

Figure 15:
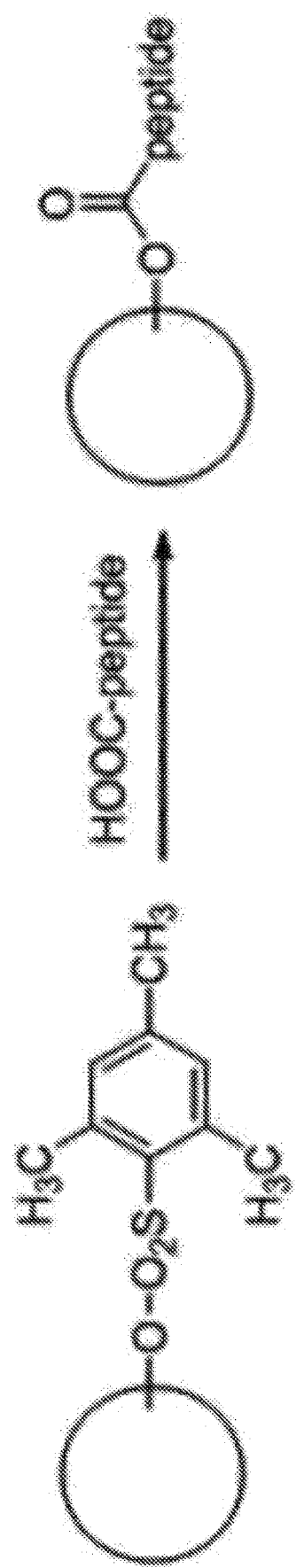
FIG. 15. Activation of dextran-based carrier for direct ester formation of carboxypeptides.

FIG. 15 shows non-bridged carbamate linkage of dicarboxy peptides to hydroxylated carbohydrates, as activated by trimethylbenzenesulfonyl chloride (MsCl). This yields ester prodrugs of the peptides having short half-lives, compared to bridged forms (FIG. 14). When carrier particles have uncharged surface groups as in polysaccharides like dextran or in hydroxylated dendrimers, amino groups of the amino alcohol linkers can be stably linked to surface hydroxyl groups as carbamates. The peptides can be released from the particles via ester hydrolysis of the ester bond between the carboxy-peptides and the amino alcohol linkers. FIG. 15 shows direct esterification of a carboxypeptide to activated hydroxyl groups of a polymer. Esters obtained by this method are expected to have short half-lives, while secondary amino-alcohol esters, which may be bridged to carriers as carbamates or amides, show half-lives of ester release ranging from weeks to months. In FIG. 15, mesyl or tosyl chlorides are used to charge sugar monomer OH groups. Mesyl/Tosyl groups are then displaced, enabling attachment of dicarboxypeptides.

Example 3—Peptide Synthesis

Peptides were synthesized in the Simpson Querrey Institute's Peptide Synthesis Core at Northwestern University. Peptide synthesis was carried out using a CEM Liberty microwave-assisted peptide synthesizer via standard 9-fluorenyl methoxycarbonyl (Fmoc) solid-phase peptide synthesis on rink amide MBHA resin. Peptides were purified by reverse-phase HPLC on a Varian Prostar 210 HPLC using a water/acetonitrile (each containing 0.1% v/v trifluoroacetic acid) gradient. Eluting fractions containing the desired peptide were confirmed by mass spectrometry using an Agilent 6520 LCMS. Confirmed fractions were pooled and the acetonitrile was removed by rotary evaporation before freezing and lyophilization. Purity of lyophilized products was tested by analytical HPLC on an Agilent 1200 HPLC.

For peptides HOOC-(CH$_2$)$_3$-CO-Sar-GYNLYRVRS-CONH2 (SEQ ID NO:4) and HOOC-(CH$_2$)$_3$-CO-Sar-GYDLYRVRS-CONH$_2$ (SEQ ID NO:4) (where Sar is sarcosine), the n-terminal pentanoic acid was introduced after removal from the automated synthesizer (HN-Sar-GYNLYRVRS-resin (SEQ ID NO:4) or HN-Sar-GYDLYRVRS-resin (SEQ ID NO:4)) via a manual coupling of 5-(tert-Butoxy)-5-oxopentanoic acid (2 equiv. relative to peptide) using HATU (1.9 equiv.) and DIEA (4 equiv.), shaken for 4 h in DMF.

For peptides HOOC-C(CH$_3$)$_2$-(CH$_2$)$_2$-CO-Sar-Peg4-Sar-GYNLYRVRS-CONH$_2$ (SEQ ID NO:4) and HOOC-C(CH$_3$)$_2$-(CH$_2$)$_2$-CO-Sar-Peg4-RRYR-CONH$_2$ (where Peg4 is 15-amino-4,7,10,13-tetraoxapentadecanoic acid), the n-terminal HOOC-C(CH$_3$)$_2$-(CH$_2$)$_2$-CO-Sar-Peg4 was introduced after removal from the automated synthesizer (HN-Sar-GYNLYRVRS-resin (SEQ ID NO:4) or H2N-RRYR-resin) via the following manual additions. 15-amino-N-(9-fluorenylmethoxycarbonyl)-4,7,10,13-tetraoxapentadecanoic acid (2 equiv. relative to peptide) was coupled using HATU (1.9 equiv.) and DIEA (4 equiv.), shaken for 3 h in DMF. After removal of the Fmoc with 30% (v/v) 4-methylpiperidine in DMF for 30 min, Fmoc-sarcosine-OH (4 equiv. relative to peptide) was added with HBTU (3.9 equiv.) and DIEA (8 equiv.) and shaken in DMF for 3 h. Removal of the Fmoc was again performed with the above 4-methylpiperidine solution before adding 2,2-dimethylglutaric anhydride (2 equiv. relative to peptide) and DIEA (8 equiv.), which was shaken for 3 h or overnight in DMF.

Example 4—Synthesis of Aminoalkoxy Esters of Glutaric Acid or Adipic Acid as Bridge Structures Synthesis of Methyl 5-[(2-tert-butoxy-2-oxoethyl)(methyl)amino]-5-oxopentanoate (Cmpd. 1)

One equivalent of Sarcosine tert-butyl ester hydrochloride was dissolved in dichloromethane (DCM) with two equivalents of triethylamine (TEA) under stirring at room temperature. Then one equivalent of glutaric acid chloride monomethyl ester is dissolved in DCM and this solution is added dropwise into the first solution. After 30 minutes, and solvent removal under vacuum, the crude product is purified by column chromatography (CC) on silica gel (Davisil), eluting with a mixture of DCM:methanol.

Product Cmpd. 1:

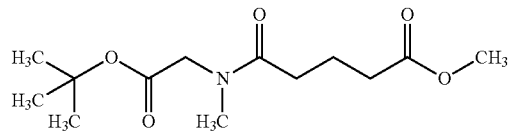 [SMILES: COC(=O)CCCC(=O)N(C)CC(=O)OC(C)(C)C]

Transparent oil. $^1$H NMR (500 MHz, Chloroform-d) δ 4.16 (s, 1H), 3.64 (s, 2H), 3.12 (s, 2H), 2.90 (t, J=5.4 Hz, 1H), 2.35 (t, J=5.5 Hz, 1H), 1.96 (p, J=5.5 Hz, 1H), 1.43 (s, 5H).

2. Synthesis of Potassium 5-[(2-tert-butoxy-2-oxoethyl)(methyl)amino]-5-oxopentanoate (Cmpd. 2)

One equivalent of cmpd. 1 is dissolved in a mixture of methanol:water 1:1. Then, 1 equivalent of potassium hydroxide is added to the first solution. Ester hydrolysis is complete after stirring, at room temperature for 30 minutes. This solution is extracted with water:chloroform. The aqueous phase is evaporated under vacuum to give the potassium salt.

Product Cmpd. 2:

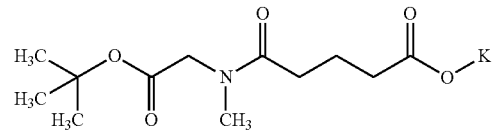

Yellowish oil. $^1$H NMR (500 MHz, DMSO-d6) δ 4.11 (s, 1H), 2.96 (s, 2H), 2.32 (t, J=7.1 Hz, 1H), 2.27 (t, J=7.1 Hz, 1H), 2.02 (p, J=7.1 Hz, 1H), 1.42 (s, 5H).

3. Synthesis of 4-{[(tert-butoxy)carbonyl]amino}butyl 4-{[2-(tert-butoxy)-2-oxoethyl](methyl) carbamoyl}butanoate (Cmpd. 3)

One equivalent of cmpd. 1 is dissolved in toluene under stirring at azeotropic reflux, mixed with a 6% of trioctylphosphine dimethylcarbonate and a 3% of lanthanum(III) nitrate and 1.5 equivalents of 4-(Boc-amino)-1-butanol. After 6 hours the reaction is complete, solvent removed under vacuum and product purified by silica gel chromatography with a mixture of n-hexane:chloroform:methanol.

Product Cmpd. 3:

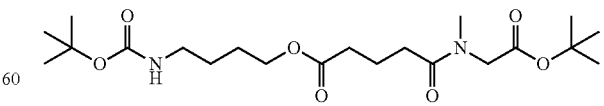

Yellowish oil. $^1$H NMR (500 MHz, Chloroform-d) δ 5.34 (br, s 1H), 4.18-4.12 (m, 2H), 3.24 (t, J=7.5 Hz, 1H), 3.09 (s, 2H), 2.90 (t, J=5.4 Hz, 1H), 2.35 (t, J=8.1 Hz, 1H), 1.96 (tt, J=8.1, 5.3 Hz, 1H), 1.82-1.72 (m, 1H), 1.68 (tt, J=7.6, 5.5 Hz, 1H), 1.43 (d, J=4.9 Hz, 9H).

4. Synthesis of 2-[5-(4-{[(tert-butoxy)carbonyl]amino}butoxy)-N-methyl-5-oxopentanamido] acetic Acid (Cmpd. 4)

One equivalent of cmpd. 3 is dissolved in a mixture of DCM:trifluoroacetic acid 95:5 v:v at room temperature. After two hours BOC ester removal is complete, after which the solution is diluted with a large volume of toluene and rotary evaporated using a 40-50° water bath.
Product Cmpd 4:

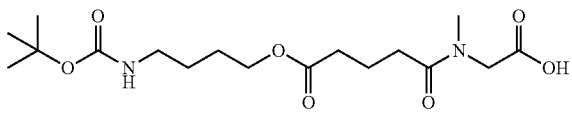 [SMILES: CN(CC(=O)O)C(=O)CCCC(=O)OCCCCNC(=O)OC(C)(C)C]

Yellowish oil. $^1$H NMR (500 MHz, DMSO-d6) δ 7.13 (s, 1H), 4.15-4.07 (m, 2H), 3.09-3.01 (m, 3H), 2.39-2.28 (m, 2H), 2.19-2.09 (m, 1H), 1.65-1.49 (m, 2H), 1.39 (s, 5H).

5. Synthesis of 4-{[(tert-butoxy)carbonyl]amino}cyclohexyl 4-{[2-(tert-butoxy)-2-oxoethyl](methyl)carbamoyl}butanoate (Cmpd. 5)

One equivalent of cmpd. 1 is dissolved in toluene, with stirring at azeotropic reflux, mixed with 10% of Pentafluorophenylammonium triflate (PFPAT) and 1.5 equivalents of trans-4-(Boc-amino)cyclohexanol. After 6 days the reaction is complete. The mixture is dried under vacuum and purify it by silica gel chromatography, eluting with a mixture of n-hexane:chloroform:methanol.
Product Cmpd. 5:

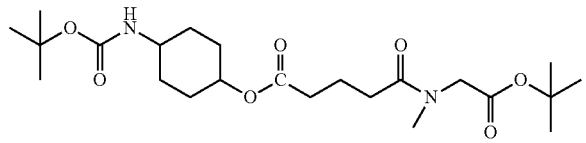 [SMILES: CN(CC(=O)OC(C)(C)C)C(=O)CCCC(=O)OC1CCC(NC(=O)OC(C)(C)C)CC1]

Yellowish oil. $^1$H NMR (500 MHz, Chloroform-d) δ 4.45 (s, 1H), 4.16 (s, 2H), 3.06 (s, 3H), 2.90 (t, J=5.4 Hz, 2H), 2.35 (t, J=5.4 Hz, 2H), 2.04-1.92 (m, 6H), 1.67-1.57 (m, 2H), 1.43 (d, J=4.9 Hz, 20H).

6. Synthesis of 2-{5-[(4-{[(tert-butoxy)carbonyl]amino}cyclohexyl)oxy]-N-methyl-5-oxopentanamido}acetic Acid (Cmpd. 6)

One equivalent of cmpd. 5 is dissolved in a mixture of DCM:trifluoroacetic acid 95:5 v:v at room temperature. After two hours Sar-BOC ester removal is complete, the solution is diluted with 10 volumes of toluene and dried by rotary evaporation with mild heating (<50° C.). This product is then provided for N-terminal capping of a peptide attached to resin for solid state peptide synthesis.
Product Cmpd. 6:

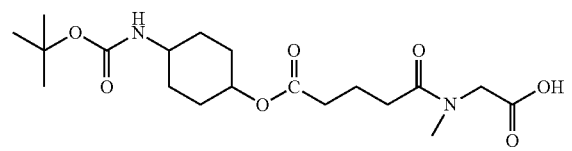 [SMILES: CN(CC(=O)O)C(=O)CCCC(=O)OC1CCC(NC(=O)OC(C)(C)C)CC1]

Yellowish oil. $^1$H NMR (500 MHz, Chloroform-d) δ 4.50-4.38 (m, 1H), 4.14 (s, 1H), 3.02 (s, 2H), 2.90 (t, J=5.4 Hz, 1H), 2.35 (t, J=8.1 Hz, 1H), 2.08-1.91 (m, 3H), 1.64 (dq, J=11.7, 6.7, 6.1 Hz, 1H), 1.56-1.43 (m, 1H), 1.44 (s, 5H).

7. Synthesis of Tert-Butyl 4-[(4-{[2-(tert-butoxy)-2-oxoethyl](methyl)carbamoyl}butanoyl)oxy] piperidine-1-carboxylate (Cmpd. 7)

One equivalent of cmpd. 2 and 0.1 equivalents of 18-crown-6 (phase transfer catalyst) are dissolved in a mixture of dimethyl sulfoxide:toluene 2:8 v:v, with stirring at 40° C. After 30 minutes, 1.1 equivalents of 1-Boc-4-bromopiperidine and 0.1 equivalents of 4-Dimethylaminopyridine (DMAP) are added. After 18 hours the reaction is dried under vacuum.

Crude product is stirred with water:chloroform. After water removal and a second water wash the organic phase is concentrated under vacuum and purified by silica gel chromatography, eluting with a mixture of n-hexane:chloroform:methanol.
Product Cmpd. 7:

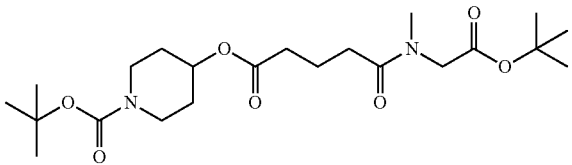 [SMILES: CN(CC(=O)OC(C)(C)C)C(=O)CCCC(=O)OC1CCN(C(=O)OC(C)(C)C)CC1]

Yellowish oil $^1$H NMR (500 MHz, Chloroform-d) δ 4.69 (m, 1H), 4.18-4.09 (m, 2H), 3.23 (dt, J=12.5, 7.2 Hz, 1H), 3.16 (s, 2H), 2.90 (t, J=8.0 Hz, 1H), 2.35 (t, J=5.4 Hz, 1H), 2.08-1.82 (m, 3H), 1.45 (d, J=20.0 Hz, 9H).

8. Synthesis of 2-[5-({1-[(tert-butoxy)carbonyl]piperidin-4-yl}oxy)-N-methyl-5-oxopentanamido] acetic Acid (Cmpd. 8)

One equivalent of cmpd. 7 is dissolved in a mixture of DCM:trifluoroacetic acid 95:5 at room temperature. Sar-BOC ester removal is complete after 2 hours, after which the solution is diluted with a large volume of toluene and dried by rotary evaporation with mild heating.
Product Cmpd. 8:

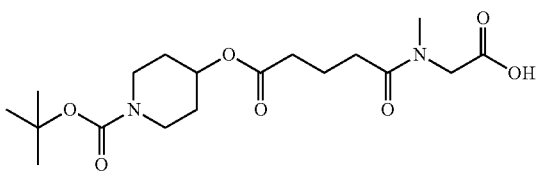 [SMILES: CN(CC(=O)O)C(=O)CCCC(=O)OC1CCN(C(=O)OC(C)(C)C)CC1]

Yellowish oil. $^1$H NMR (500 MHz, DMSO-d6) δ 4.76 (m, 1H), 4.09 (s, 1H), 4.03 (dt, J=12.5, 7.0 Hz, 1H), 3.11 (dt, J=12.6, 7.1 Hz, 1H), 2.96 (s, 2H), 2.39-2.28 (m, 2H), 2.19-2.09 (m, 1H), 1.92-1.81 (m, 1H), 1.58 (dq, J=14.1, 7.1 Hz, 1H), 1.42 (s, 5H).

9. Synthesis of 3-{[(tert-butoxy)carbonyl]amino}cyclopentyl 4-{[2-(tert-butoxy)-2-oxoethyl](methyl) carbamoyl}butanoate (Cmpd. 9)

One equivalent of cmpd. 1 is dissolved in toluene, with stirring at azeotropic reflux, and mixed with 10 mol % of Pentafluorophenylammonium triflate (PFPAT) and 1.5 equivalents of N-[(1R, 3R)-3-hydroxycyclopentyl]-, 1,1-dimethylethyl ester. After 6 days the trans-esterification is complete. The mixture is dried under vacuum, dissolved in 3 ml chloroform and purified by elution through silica gel with a mixture of n-hexane:chloroform:methanol.

Product Cmpd. 9:

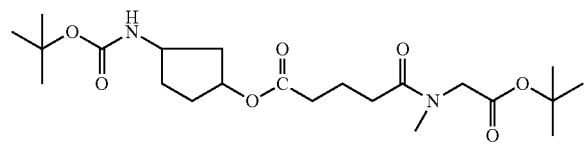 [SMILES: CN(CC(=O)OC(C)(C)C)C(=O)CCCC(=O)OC1CCC(NC(=O)OC(C)(C)C)C1]

Yellowish oil. $^1$H NMR (500 MHz, Chloroform-d) δ 5.12 (d, J=12.3 Hz, 1H), 4.96 (p, J=7.0 Hz, 1H), 4.56 (s, 1H), 3.81-3.70 (m, 2H), 3.16 (td, J=12.5, 3.2 Hz, 1H), 3.10 (s, 3H), 2.61 (td, J=12.4, 1.5 Hz, 1H), 2.34 (qdd, J=12.3, 3.2, 1.6 Hz, 1H), 2.30-2.11 (m, 5H), 2.03 (dq, J=12.7, 7.0 Hz, 1H), 1.78-1.52 (m, 3H), 1.43 (d, J=4.9 Hz, 18H).

10. Synthesis of 2-{5-[(3-{[(tert-butoxy)carbonyl]amino}cyclopentyl)oxy]-N-methyl-5-oxopentanamido}acetic Acid (Cmpd. 10)

One equivalent of cmpd. 9 is dissolved in a mixture of DCM:trifluoroacetic acid 95:5 at room temperature, de-blocking the Sar-BOC ester in two hours. The solution is diluted with a large volume of toluene and evaporated under vacuum with mild heating.

Product Cmpd 10:

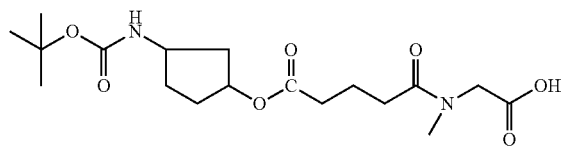 [SMILES: CN(CC(=O)O)C(=O)CCCC(=O)OC1CCC(NC(=O)OC(C)(C)C)C1]

Yellowish oil $^1$H NMR (500 MHz, Chloroform-d) δ 4.87 (p, J=6.9 Hz, 1H), 4.70 (d, J=12.4 Hz, 1H), 4.24 (s, 1H), 4.06 (p, J=7.0 Hz, 1H), 3.98 (d, J=12.5 Hz, 1H), 3.01 (s, 3H), 2.95 (ddd, J=12.5, 4.7, 1.8 Hz, 1H), 2.65-2.50 (m, 2H), 2.31 (td, J=12.5, 2.5 Hz, 1H), 2.24-2.12 (m, 2H), 2.06-1.94 (m, 1H), 1.95-1.83 (m, 2H), 1.78 (dt, J=13.0, 7.1 Hz, 1H), 1.60-1.45 (m, 2H), 1.44 (s, 9H).

11. Synthesis of Methyl 6-[(2-tert-butoxy-2-oxo-ethyl)amino]-6-oxohexanoate (Cmpd. 11)

One equivalent of Glycine tert-butyl ester hydrochloride is dissolved in dichloromethane (DCM) with two equivalents of triethylamine under stirring at room temperature. Then one equivalent of Adipic acid monomethyl ester chloride is dissolved in DCM and this solution is added dropwise on the first solution. After 30 minutes the reaction mixture is concentrated by evaporation, dissolved in 2-4 ml CHCl3 and the product is purified by column chromatography (silica gel, Davisil) with a mixture of DCM:methanol.

Product Cmpd. 11:

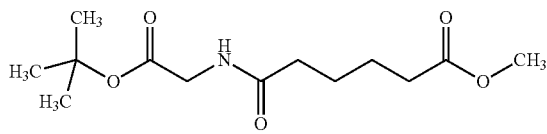 [SMILES: COC(=O)CCCCC(=O)NCC(=O)OC(C)(C)C]

Yellowish oil. $^1$H NMR (500 MHz, Chloroform-d) δ 6.73 (s, TH), 4.17 (s, TH), 3.64 (s, 2H), 2.52 (t, J=8.0 Hz, TH), 2.35 (t, J=8.1 Hz, TH), 1.77-1.67 (m, TH), 1.61 (pd, J=7.9, 1.1 Hz, TH), 1.43 (s, 5H).

12. Synthesis of Potassium 6-[(2-tert-butoxy-2-oxo-ethyl)amino]-6-oxohexanoate (Cmpd. 12)

One equivalent of cmpd. 11 is dissolved in a mixture of methanol:water 1:1. Then, 1 equivalent of potassium hydroxide is added to the first solution. Conditions: stirring, room temperature. After 30 minutes methyl ester hydrolysis is complete.

Crude product is washed in a separatory funnel with water:chloroform, the aqueous phase is evaporated under vacuum.

Product Cmpd. 12:

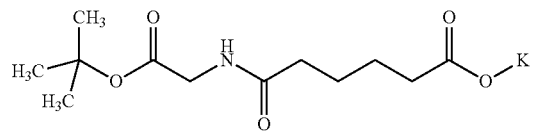

Yellowish oil. $^1$H NMR (500 MHz, DMSO-d6) δ 8.49 (s, TH), 4.17 (s, 2H), 2.30-2.24 (m, 2H), 2.16-2.10 (m, TH), 2.13 (s, TH), 1.56-1.45 (m, 4H), 1.42 (s, 9H).

13. Synthesis of Tert-Butyl 3-[(5-{[2-(tert-butoxy)-2-oxoethyl]carbamoyl}pentanoyl)oxy]pyrrolidine-1-carboxylate (Cmpd. 13)

One equivalent of the Comp 12 and 0.1 equivalents of 18-crown-6 are dissolved in a mixture of dimethyl sulfoxide:toluene 2:8. And stirred at 40° C. After 30 minutes, 1.1 equivalents of 1-Boc-3-bromopyrrolidine and 0.1 equivalents of DMAP are added. After 18 hours the reaction is stopped and dried under vacuum, the residue dissolved in CHCl3. This is washed in a separatory funnel with water:chloroform. The organic phase is concentrated under vacuum and purified by silica gel chromatography, eluting with a mixture of n-hexane:chloroform:methanol.

Product Cmpd. 13:

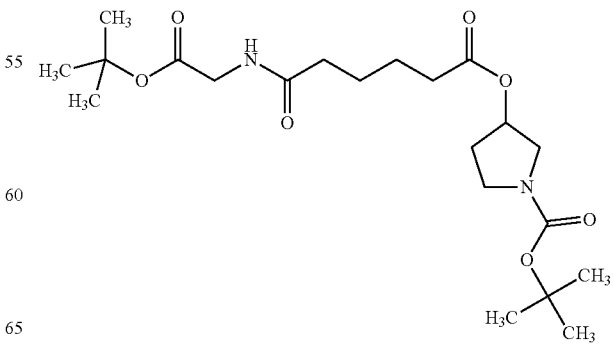

Yellowish oil. ¹H NMR (500 MHz, Chloroform-d) δ 6.73 (s, 1H), 4.96 (p, J=7.1 Hz, 1H), 4.90 (d, J=12.3 Hz, 1H), 4.04 (dd, J=9.4, 7.1 Hz, 1H), 3.94 (d, J=12.3 Hz, 1H), 3.80 (dt, J=9.5, 7.1 Hz, 1H), 3.44-3.35 (m, 2H), 3.04-2.88 (m, 2H), 2.67 (td, J=12.4, 4.2 Hz, 1H), 2.23 (dq, J=13.8, 7.0 Hz, 1H), 2.21-2.08 (m, 1H), 2.11-1.90 (m, 3H), 1.45 (d, J=20.0 Hz, 18H).

14. Synthesis of 2-[6-({1-[(tert-butoxy)carbonyl]pyrrolidin-3-yl}oxy)-6-oxohexanamido]acetic Acid (Cmpd 14)

One equivalent of cmpd. 13 is dissolved in a mixture of DCM:trifluoroacetic acid 95:5 v:v at room temperature for 2 h, completely removing the Gly-t-But ester. The solution is diluted with 10 volumes of toluene and dried by rotary evaporation with mild heating.

Product Cmpd. 14

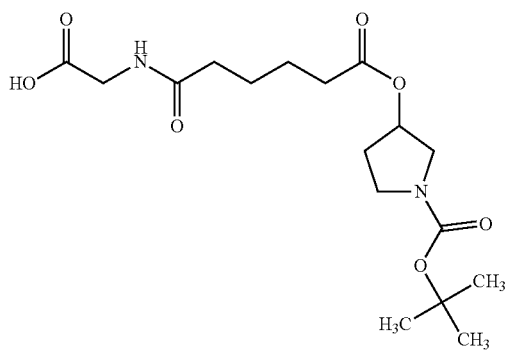 [SMILES: CC(C)(C)OC(=O)N1CCC(OC(=O)CCCCC(=O)NCC(=O)O)C1]

Yellowish oil. ¹H NMR (500 MHz, Chloroform-d) δ 6.73 (s, 1H), 4.96 (p, J=7.1 Hz, 1H), 4.17-4.09 (m, 2H), 4.05 (d, J=12.3 Hz, 1H), 3.76 (dt, J=9.5, 7.1 Hz, 1H), 3.56 (dt, J=9.3, 7.1 Hz, 1H), 3.38 (dd, J=9.4, 7.1 Hz, 1H), 2.98-2.90 (m, 1H), 2.61-2.49 (m, 1H), 2.46-2.35 (m, 2H), 2.37-2.29 (m, 1H), 2.14-2.05 (m, 1H), 1.97 (dq, J=14.1, 7.1 Hz, 1H), 1.77-1.57 (m, 3H), 1.47 (s, 9H).

15. Synthesis of 9H-fluoren-9-ylmethyl N-(4-hydroxycyclohexyl)carbamate (Cmpd. 15)

One equivalent of trans-4-aminocyclohexanol hydrochloride is dissolved in DCM with two equivalents of TEA, and stirred in an ice bath. Then one equivalent of 9-Fluorenylmethyl chloroformate (Fmoc-Cl) is dissolved in DCM and this solution is added dropwise to the first solution, reaction at room temperature being complete in 24 h.

After adding 5 volumes of CHCl3 crude product is washed in a separatory funnel with water, organic phase is evaporated under vacuum. Crude product re-dissolved in a small volume of CHCl3 was then purified by silica gel chromatography, eluting with a mixture of n-hexane:chloroform:methanol.

Product Cmpd. 15:

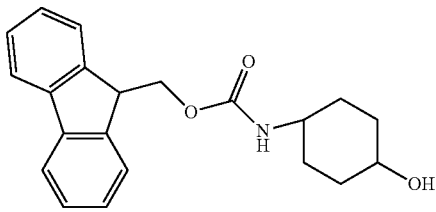 [SMILES: O=C(NC1CCC(O)CC1)OCC1c2ccccc2-c2ccccc21]

White powder. ¹H NMR (500 MHz, Chloroform-d) δ 7.81 (dd, J=7.4, 1.6 Hz, 2H), 7.59-7.49 (m, 4H), 7.43 (td, J=7.5, 1.5 Hz, 2H), 4.70 (d, J=5.8 Hz, 2H), 4.50 (s, 1H), 4.37 (t, J=5.8 Hz, 1H), 3.74-3.63 (m, 2H), 2.10-1.93 (m, 4H), 1.73-1.59 (m, 4H), 1.54 (s, 1H).

16. Synthesis of 9H-fluoren-9-ylmethyl N-(4-bromocyclohexyl)carbamate (Cmpd. 16)

One equivalent of cmpd. 15 is dissolved in dry tetrahydrofuran (THF) with one equivalent of tetrabromomethane, and stirred at room temperature, when the compounds are dissolved 1.0 equivalent of ethylenebis(diphenylphosphine) is added.reaction is complete in 3 hours, after which the solution is filtered and the crude product is purified by silica gel chromatography, eluting with a mixture of n-hexane:chloroform:methanol.

Product Cmpd. 16:

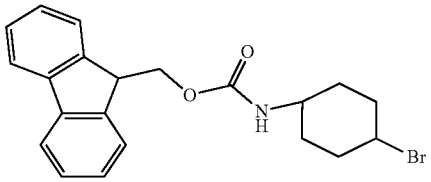 [SMILES: O=C(NC1CCC(Br)CC1)OCC1c2ccccc2-c2ccccc21]

White powder ¹H NMR (500 MHz, Chloroform-d) δ 7.80 (dd, J=7.4, 1.6 Hz, 2H), 7.58-7.49 (m, 4H), 7.43 (td, J=7.4, 1.6 Hz, 2H), 4.73-4.65 (m, 3H), 4.64 (q, J=7.0 Hz, 1H), 4.27 (t, J=5.8 Hz, 1H), 4.11 (p, J=7.0 Hz, 1H), 2.22 (dq, J=12.2, 6.9 Hz, 2H), 2.04-1.87 (m, 4H), 1.60 (dq, J=12.8, 6.9 Hz, 2H).

17. Synthesis of 4-[(9H-Fluoren-9-yl)methoxycarbonylamino]cyclohexyl 5-[N-methyl(tert-butoxycarbonylmethyl)amino]-5-oxovalerate (Cmpd. 17)

One equivalent of the cmpd. 2 and 0.1 equivalents of 18-crown-6 are dissolved in a mixture of dimethyl sulfoxide:toluene 2:8 v:v, with stirring at 40° C. After 30 minutes, 1.1 equivalents of cmpd 16 are added. After 18 hours the reaction is stopped and dried under vacuum. Crude product dissolved in CHCl3 is washed in a separatory funnel with water:chloroform, the organic phase concentrated by evaporation, then purified by silica gel chromatography, developed by a mixture of n-hexane:chloroform:methanol.

Product Cmpd. 17:

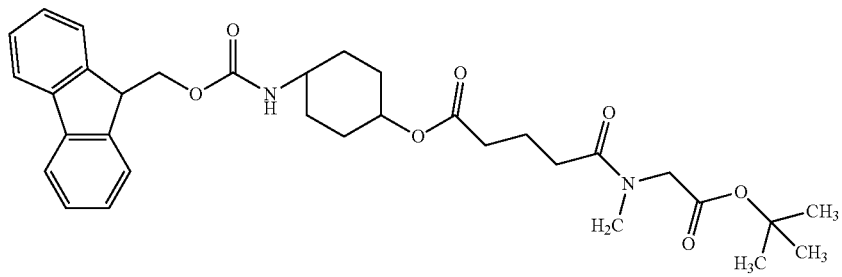 [SMILES: CN(CC(=O)OC(C)(C)C)C(=O)CCCC(=O)OC1CCC(NC(=O)OCC2c3ccccc3-c3ccccc32)CC1]

¹H NMR (500 MHz, Chloroform-d) δ 7.83-7.75 (m, 3H), 7.56-7.39 (m, 5H), 4.70 (d, J=7.0 Hz, 2H), 4.64 (s, 1H), 4.40 (p, J=6.9 Hz, 1H), 4.28 (t, J=7.0 Hz, 1H), 4.16 (s, 2H), 3.72 (p, J=6.9 Hz, 1H), 3.12 (s, 3H), 2.90 (t, J=5.4 Hz, 2H), 2.35 (t, J=8.2 Hz, 2H), 2.11-1.90 (m, 6H), 1.73-1.62 (m, 2H), 1.65-1.51 (m, 2H), 1.43 (s, 9H).

18. Synthesis of [N-Methyl(4-{4-[(9H-fluoren-9-yl)methoxycarbonylamino]cyclohexyloxycarbonyl}butyryl)amino]acetic Acid (Cmpd. 18)

One equivalent of cmpd. 17 is dissolved in a mixture of DCM:trifluoroacetic acid 95:5 at room temperature, after 2 hours t-butyl ester removal is complete. The solution is diluted with 10 volumes of toluene and dried by rotary evaporation with gentle heating.

Product Cmpd. 18:

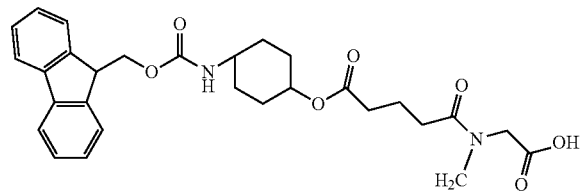 [SMILES: CN(CC(=O)O)C(=O)CCCC(=O)OC1CCC(NC(=O)OCC2c3ccccc3-c3ccccc32)CC1]

¹H NMR (500 MHz, DMSO-d6) δ 7.79 (dd, J=7.5, 1.7 Hz, 2H), 7.64 (dd, J=7.4, 1.5 Hz, 2H), 7.54 (td, J=7.5, 1.6 Hz, 2H), 7.50-7.39 (m, 3H), 4.70 (d, J=7.1 Hz, 2H), 4.38 (p, J=7.0 Hz, 1H), 4.20 (t, J=7.1 Hz, 1H), 4.09 (s, 2H), 3.85 (p, J=7.0 Hz, 1H), 2.89 (s, 3H), 2.34 (dt, J=19.7, 5.3 Hz, 4H), 2.14 (p, J=5.3 Hz, 2H), 2.02 (dq, J=12.7, 7.0 Hz, 2H), 1.70-1.59 (m, 2H), 1.60-1.49 (m, 2H), 1.26 (dq, J=13.0, 7.1 Hz, 2H).

In solid state peptide synthesis compound 18 is linked to the growing peptide chain (eg: side chain blocked G-Y-N-L-Y-R-V-R-S-resin) (SEQ ID NO: 4) linked to amide resin by standard coupling procedures. FMOC is then removed by 15 minute exposure to 30% 4-methylpiperidine in DMF, after which blocking groups and peptide are released by TFA to give 4-amino-cyclohexanol-esterified SEQ ID 4 for carbamate or amide coupling to carriers.

REFERENCES

Funatomi, T., Wakasugi, K., Misaki, T., & Tanabe, Y. (2006). "Pentafluorophenylammonium triflate (PFPAT), an efficient, practical, and cost-effective catalyst for esterification, thioesterification, transesterification, and macrolactone formation," Green Chemistry, 8(12), 1022-1027.

Stott, P. E., Bradshaw, J. S., & Parish, W. W. (1980), "Modified crown ether catalysts. 3. Structural parameters affecting phase transfer catalysis by crown ethers and a comparison of the effectiveness of crown ethers to that of other phase transfer catalysts," Journal of the American Chemical Society, 102(14), 4810-4815.

Hatano, M., & Ishihara, K. (2013), "Lanthanum (III) catalysts for highly efficient and chemoselective transesterification. Chemical Communications," 49(20), 1983-1997.

Pollastri, MP., Sagal, J. F., & Chang, G. (2001). The conversion of alcohols to halides using a filterable phosphine source. Tetrahedron Letters, 42(13), 2459-2460.

Example 5—Ester Hydrolysis Testing

Compounds (BOC amido alkoxy esters) was dissolved in a solution of ethanol. This solution was diluted with different buffers with range of pH (from pH 7.33 to 8.34) to a known concentration. The sterile-filtered solutions were stored at 37° C. and were checked by high performance liquid chromatography (HPLC) over time points and the half life of the amido-alkoxy amino acid esters was calculated. (See Table 2).

TABLE 2

Half-life of amido-alkoxy amino acid esters at 37° C.

| Ester | $t_{1/2}$ (days) | | |
|---|---|---|---|
| | pH: 7.33 | pH: 7.44 | pH: 7.66 |
| BOC-but-O-glt-Sar | 20 | — | 11 |
| BOC-etOet-O-glt-Sar | 8.5 | — | — |
| BOC-pyrrol-O-adp-Gly | — | — | 30 |
| BOC-piper-O-adp-Gly | — | — | 23 |
| BOC-trans3cyclohex-O-adp-Gly | — | — | 70 |
| BOC-trans3cyclohex-O-glt-Sar | — | 27 | — |
| BOC-3cypent-O-glt-Sar | — | 29.66 | — |
| BOC-2cypent-O-glt-Sar | — | 20.97 | — |
| BOC-et-N-val-secO-glt-Sar | — | 23 | — |

Example 6—Generation of Dextran Micro- and Nano-Gels 4 g of dextran (M.w. 70,000, unit M.w. 190) was dried by co-evaporation with anhydrous pyridine in vacuo and activated by reaction with 93 mg 1,1'-carbonyldiimidazole (CDI) in 100 mL of anhydrous dimethyl sulfoxide (DMSO) at 25° C. under stirring for 4 h. Cholesteryl-amine was synthesized by modification of cholesteryl chloroformate with a 3-fold excess of 2,2'-(ethylenedioxy) bis (ethylamine) and purified by column chromatography on silicagel using a stepwise gradient of methanol in dichloromethane. 342 mg of cholesteryl-amine dissolved in 10 mL of DMSO was added to the activated dextran, and reaction mixture was stirred for 24 h at 25° C. The product (CDEX) was purified by dialysis in semi-permeable membrane tubes (MWCO 12-14,000) against water at 4° C. under stirring overnight, sonicated for 15 min and, then, freeze-dried. Total yield was 86%.

TABLE 3

| Micro/nanogel | Particle size, nm | PDI | SD | Yield, % | Treatment |
|---|---|---|---|---|---|
| CDEX | 55 (100%) | 0.27 | 4 | 86 | Sonication |

Example—7 Activation of Micro-Gels and Nano-Gels

Microgel and nanogels particles can be modified before charging with peptides or peptide intermediates using chemical activation of hydroxyl groups on dextran/dextrin with 1,1'-carbonyldiimidazole (A), with toluene or mesitylene sulfonyl chlorides (B) in order to obtain carriers, which are ready to conjugation with peptides carriers.

210 mg CDEX was dried by co-evaporation with anhydrous pyridine and mixed with 36 mg 1,1'-carbonyldiimidazole (CDI) in 10 mL anhydrous DMSO. Reaction mixture was stirred for 4 h at 40° C. The activated CDEX was purified by dialysis in semi-permeable membrane tubes (MWCO 12-14,000) against water at 4° C. under stirring overnight and, then, lyophilized. Total yield of the imidazole-activated CDEX was 69%. Proton NMR showed that 58 imidazole groups was attached to the polymer molecule (0.7 mmol imidazole moieties per 1 g).

350 mg CDEX was dried by co-evaporation with anhydrous pyridine, and 110 mg toluenesulfonyl chloride dissolved in 25 mL anhydrous DMSO along with 5 mL pyridine was added at cooling in ice bath. The reaction mixture was stirred at 25° C. overnight. Pyridine was removed in vacuo by co-evaporation with methanol. The product was purified by dialysis in semi-permeable membrane tubes (MWCO 12-14,000) against water at 4° C. under stirring overnight and recovered after freeze-drying with a yield of 75%. NMR spectrum analysis showed that 43 tosyl groups was attached to the polymer molecule (0.52 mmol tosyl moieties per Ig).

35 mg microgel was dried by co-evaporation with anhydrous pyridine and dissolved in 10 mL anhydrous DMSO-pyridine, 1:1. The mixture was cooled in ice bath, then 12 mg mesitylenesulfonyl chloride was added and the mixture was stirred at 25° C. overnight. Pyridine was removed in vacuo by co-evaporation with methanol. The product was recovered by dialysis in semi-permeable membrane tubes (MWCO 12-14 kDa) against water at 4° C. under stirring overnight and freeze-drying with total yield of 70%. NMR spectrum analysis showed that 18 molecules of mesityl groups was attached to the polymer molecule (0.22 mmol mesityl moieties per Ig).

Example 8—Conjugation of Amino-PEG-Peptides

Amino-PEG(12)-peptides containing 1, 3 or 4 arginine residues (AP1, Mw. 1,200; AP3, M.w. 1,375, and AP4, M.w. 1,550) have been conjugated with CDI-activated CDEX nanogel and investigated in biological systems. Urethane bonds formed in this reaction are stable in most biological environments.

Imidazole-activated CDEX (20 mg) was dissolved in 0.5 mL water, and pH was adjusted to 8 with sodium bicarbonate solution. 9.6 mg of a 3-Arg peptide AP3, amino-PEG(12)-CO-Arg-Arg-Ser-Arg-amide (SEQ ID NO: 16), was dissolved in 0.2 mL DMF and mixed with the CDEX solution. Reaction was continued overnight at 25° C. and, then, quenched with 5 µL ethanolamine overnight at 4° C. Carrier-peptide conjugates were purified by dialysis in semi-permeable membrane tubes (MWCO 12-14,000) against water at 4° C. under stirring overnight and, then, freeze-dried. The reaction was repeated similarly for 9.6 mg AP3, and 10.9 mg AP4.

TABLE 4

Carbamate linkage of amino-PEG peptide with 3 Arg residues

| Sample | Peptide, % | Size, nm (SD) | PDI | Z-potential, mV | Yield, % |
|---|---|---|---|---|---|
| CDEX-AP3 | 31 | 124 ± 1.4 | 0.167 | 4.58 | 58 |

Example 9—Conjugation of Carboxyl-PEG-Peptides

Carboxyl groups of peptides and their derivatives have been conjugated with tosylated CDEX nanogel and investigated in biological systems. Ester bonds formed in this reaction are biodegradable, and free peptides are slowly released in most biological environments.

Tosylated CDEX nanogels (6 and 12 mg) were dissolved in two separate vials in 0.25 and 0.5 mL DMSO, respectively, and, then, mixed with a solution of 6 mg carboxyl group-containing peptide (P868) adipic-G-V-D-alloIle-S-Q-I-R-P-ethylamide (SEQ ID NO: 17) in 0.1 mL DMF and allowed to stand at 25° C. under stirring overnight. The reaction mixture was quenched with glycine (5 mg) for 2 h at 25° C. and the product was purified by dialysis in semi-permeable membrane tubes (MWCO 12-14,000) against water at 4° C. under stirring overnight and, then, freeze-dried. Total yield: 75-80%.

TABLE 5

| Sample | Peptide, % | Size, nm (SD) | PDI | Z-potential, mV | Yield, % |
|---|---|---|---|---|---|
| CDEX-P868 high | 29 | 112 ± 4 | 0.143 | 0.253 | 80 |
| CDEX-P868 low | 18 | 121 ± 1.2 | 0.158 | 0 | 75 |

Example 10—Characterization of CDEX-Peptide Conjugates

Peptide content in carrier-peptide conjugates was measured using a Pierce BCA Protein Assay based on the calibration curve obtained with the corresponding free peptide. Peptide analysis was performed as follows: 20 mg/mL stock solution of peptide in water was used to prepare serial ½ dilutions of standards. Then, BCA working reagent (WR) was prepared by mixing 50 mL of BCA reagent A (50 mL) with 1 mL of BCA reagent B. 25 µL of each standard dilutions and a carrier-peptide conjugate sample (3-5 mg/mL) were placed into 96-well plate in triplicates, then 200 μL of WR was added to each well, and the plate was mixed thoroughly in shaker for 30 sec. Plate was covered and incubate at 37° C. for 30 min, cooled at 25° C., and the absorbance was measured at 562 nm using a plate reader. Peptide content (%) in the samples was calculated based on the calibration curve of free peptide.

Sample characteristics (particle size, polydispersity and zeta-potential) were measured by a dynamic light scattering method using Malvern Zeta Sizer Nano-S90 instrument according to the manufacturer recommendations. Briefly, hydrodynamic diameter (dh) and polydispersity index (PDI) of nanogel/microgels were obtained for 1 mg/mL aqueous solutions at 25° C. in triplicates after sonication for 30 min and centrifugation at 12,000 rpm. Zeta-potential of the samples was measured for the same solutions in standard 1 cm-cuvettesusing zeta-potential option in the company's software. Average of five measurements+SD was registered.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

```
                        SEQUENCE LISTING

<160> NUMBER OF SEQ ID NOS: 17

<210> SEQ ID NO 1
    <211> LENGTH: 9
    <212> TYPE: PRT
    <213> ORGANISM: Artificial
    <220> FEATURE:
    <223> OTHER INFORMATION: Derivative of Homo sapiens Pigment Epithelium-
          Derived Factor Peptide

<400> SEQUENCE: 1

Gly Tyr Asp Leu Tyr Arg Val Arg Ser
    1               5

<210> SEQ ID NO 2
    <211> LENGTH: 9
    <212> TYPE: PRT
    <213> ORGANISM: Artificial
    <220> FEATURE:
    <223> OTHER INFORMATION: Derivative of Homo sapiens Pigment Epithelium-
          Derived Factor Peptide

<400> SEQUENCE: 2

Gly Tyr Asp Leu Tyr Arg Val Arg Ser
    1               5

<210> SEQ ID NO 3
    <211> LENGTH: 9
    <212> TYPE: PRT
    <213> ORGANISM: Artificial
    <220> FEATURE:
    <223> OTHER INFORMATION: Derivative of Homo sapiens Pigment Epithelium-
          Derived Factor Peptide

<400> SEQUENCE: 3

Gly Tyr Asp Leu Tyr Arg Val Arg Ser
    1               5

<210> SEQ ID NO 4
    <211> LENGTH: 9
    <212> TYPE: PRT
    <213> ORGANISM: Artificial
    <220> FEATURE:
    <223> OTHER INFORMATION: Derivative of Homo sapiens Pigment Epithelium-
```

Derived Factor Peptide

<400> SEQUENCE: 4

Gly Tyr Asn Leu Tyr Arg Val Arg Ser
1               5

<210> SEQ ID NO 5
<211> LENGTH: 8
<212> TYPE: PRT
<213> ORGANISM: Artificial
<220> FEATURE:
<223> OTHER INFORMATION: Derivative of Homo sapiens Pigment Epithelium-
      Derived Factor Peptide

<400> SEQUENCE: 5

Tyr Asn Leu Tyr Arg Val Arg Ser
1               5

<210> SEQ ID NO 6
<211> LENGTH: 9
<212> TYPE: PRT
<213> ORGANISM: Artificial
<220> FEATURE:
<223> OTHER INFORMATION: Derivative of Homo sapiens Pigment Epithelium-
      Derived Factor Peptide

<400> SEQUENCE: 6

Gly Tyr Asn Leu Tyr Arg Val Arg Ser
1               5

<210> SEQ ID NO 7
<211> LENGTH: 9
<212> TYPE: PRT
<213> ORGANISM: Artificial
<220> FEATURE:
<223> OTHER INFORMATION: Derivative of Homo sapiens Pigment Epithelium-
      Derived Factor Peptide

<400> SEQUENCE: 7

Gly Tyr Asn Leu Tyr Arg Val Arg Ser
1               5

<210> SEQ ID NO 8
<211> LENGTH: 8
<212> TYPE: PRT
<213> ORGANISM: Artificial
<220> FEATURE:
<223> OTHER INFORMATION: Derivative of Homo sapiens Pigment Epithelium-
      Derived Factor Peptide

<400> SEQUENCE: 8

Gly Tyr Asn Leu Tyr Arg Val Pro
1               5

<210> SEQ ID NO 9
<211> LENGTH: 8
<212> TYPE: PRT
<213> ORGANISM: Artificial
<220> FEATURE:
<223> OTHER INFORMATION: Derivative of Homo sapiens Pigment Epithelium-
      Derived Factor Peptide

<400> SEQUENCE: 9

Tyr Asn Leu Tyr Arg Val Gln Ser
1               5

<210> SEQ ID NO 10

```
<211> LENGTH: 7
<212> TYPE: PRT
<213> ORGANISM: Artificial
<220> FEATURE:
<223> OTHER INFORMATION: Derivative of Homo sapiens Pigment Epithelium-
      Derived Factor Peptide

<400> SEQUENCE: 10

Tyr Asn Leu Tyr Arg Val Pro
1               5

<210> SEQ ID NO 11
<211> LENGTH: 8
<212> TYPE: PRT
<213> ORGANISM: Artificial
<220> FEATURE:
<223> OTHER INFORMATION: Derivative of Homo sapiens Pigment Epithelium-
      Derived Factor Peptide

<400> SEQUENCE: 11

Tyr Asn Leu Tyr Arg Val Arg Ser
1               5

<210> SEQ ID NO 12
<211> LENGTH: 6
<212> TYPE: PRT
<213> ORGANISM: Artificial
<220> FEATURE:
<223> OTHER INFORMATION: Derivative of Homo sapiens Pigment Epithelium-
      Derived Factor Peptide

<400> SEQUENCE: 12

Asn Leu Tyr Arg Val Pro
1               5

<210> SEQ ID NO 13
<211> LENGTH: 7
<212> TYPE: PRT
<213> ORGANISM: Artificial
<220> FEATURE:
<223> OTHER INFORMATION: Derivative of Homo sapiens Pigment Epithelium-
      Derived Factor Peptide

<400> SEQUENCE: 13

Asn Leu Tyr Arg Val Arg Ser
1               5

<210> SEQ ID NO 14
<211> LENGTH: 11
<212> TYPE: PRT
<213> ORGANISM: Artificial
<220> FEATURE:
<223> OTHER INFORMATION: Modified amino acid sequence of human Pigment
      Epithelium-Derived Factor (PEDF) peptide
<220> FEATURE:
<221> NAME/KEY: MISC_FEATURE
<223> OTHER INFORMATION: X is selected from a naturally occurring amino
      acid, including sarcosine, or beta alanine
<220> FEATURE:
<221> NAME/KEY: MISC_FEATURE
<223> OTHER INFORMATION: X in the 0 position is absent or present, and
      when X in the 0 position is present, X in the 0 position is
      selected from sarcosine, Gly, or beta alanine
<220> FEATURE:
<221> NAME/KEY: MISC_FEATURE
<223> OTHER INFORMATION: X in position 1 is absent or present, and when
      X in position 1 is present, X in position 1 is selected from
      sarcosine and Gly
```

```
<220> FEATURE:
<221> NAME/KEY: MISC_FEATURE
<223> OTHER INFORMATION: X in position 2 is absent or present, and when
      X in position 2 is present, X in position 2 is Tyr
<220> FEATURE:
<221> NAME/KEY: MISC_FEATURE
<223> OTHER INFORMATION: X in position 3 is Asp or Asn
<220> FEATURE:
<221> NAME/KEY: MISC_FEATURE
<223> OTHER INFORMATION: X in position 4 is Leu or Val
<220> FEATURE:
<221> NAME/KEY: MISC_FEATURE
<223> OTHER INFORMATION: X in posistion 5 is Tyr or Phe
<220> FEATURE:
<221> NAME/KEY: MISC_FEATURE
<223> OTHER INFORMATION: X in position 6 is Arg
<220> FEATURE:
<221> NAME/KEY: MISC_FEATURE
<223> OTHER INFORMATION: X in positiion 7 is Val or Pro
<220> FEATURE:
<221> NAME/KEY: MISC_FEATURE
<223> OTHER INFORMATION: X in position 8 is present or absent and when X
      in position 8 is present, X in position 8 is selected from Argu,
      Pro and Gln
<220> FEATURE:
<221> NAME/KEY: MISC_FEATURE
<223> OTHER INFORMATION: X in position 9 is present or absent and when
      present X in position 9 is selected from Ser and Ala
<220> FEATURE:
<221> NAME/KEY: MISC_FEATURE
<223> OTHER INFORMATION: X in position 10 is absent or present and when
      present X in position 10 is selected from Ser, Ser-Thr,k
      Ser-Thr-Ser, Ser-Thr-Ser-Pro, and Ser-Thr-Ser-Pro-Thr
<220> FEATURE:
<221> NAME/KEY: misc_feature
<222> LOCATION: (1)..(11)
<223> OTHER INFORMATION: Xaa can be any naturally occurring amino acid

<400> SEQUENCE: 14

Xaa Xaa Xaa Xaa Xaa Xaa Xaa Xaa Xaa Xaa Xaa
1               5                   10

<210> SEQ ID NO 15
<211> LENGTH: 18
<212> TYPE: PRT
<213> ORGANISM: Artificial sequence
<220> FEATURE:
<223> OTHER INFORMATION: Synthetic

<400> SEQUENCE: 15

Asn Phe Gly Tyr Asp Leu Tyr Arg Val Arg Ser Ser Thr Ser Pro Thr
1               5                   10                  15

Thr Asn

<210> SEQ ID NO 16
<211> LENGTH: 12
<212> TYPE: PRT
<213> ORGANISM: Artificial sequence
<220> FEATURE:
<223> OTHER INFORMATION: Synthetic

<400> SEQUENCE: 16

Ala Arg Gly Ala Arg Gly Ser Glu Arg Ala Arg Gly
1               5                   10

<210> SEQ ID NO 17
<211> LENGTH: 9
<212> TYPE: PRT
<213> ORGANISM: Artificial sequence
<220> FEATURE:
<223> OTHER INFORMATION: Synthetic
```

```
<400> SEQUENCE: 17

Gly Val Asp Ile Ser Gln Ile Arg Pro
1               5
```

We claim:

1. A modified peptide comprising:
   (a) a peptide consisting of an amino acid of AA0-AA1-AA2-AA3-AA4-AA5-AA6-AA7-AA8-AA9-AA10 (SEQ ID NO:14), wherein:
   AA0 is absent or present and when AA0 is present AA0 is selected from the group consisting of sarcosyl and Gly;
   AA1 is absent or present and when AA1 is present AA1 is selected from the group consisting of sarcosyl and Gly;
   AA2 is Tyr;
   AA3 is Asn;
   AA4 is Leu, Ile, or Val;
   AA5 is Tyr or Phe;
   AA6 is Arg;
   AA7 is Val or Pro;
   AA8 is present or absent and when AA8 is present AA8 is selected from the group consisting of Arg, Pro, and Gln;
   AA9 is present or absent and when AA9 is present AA9 is selected from the group consisting of Ser and Ala; and
   AA10 is absent or present and when AA10 is present AA10 is selected from the group consisting of Ser and Ser-Thr; and
   (b) one or more non-amino acid moieties on the N-terminal and/or C-terminal end of the peptide, wherein one of said one or more non-amino acid moieties comprises Z-B-X- linked to the N-terminal amino acid, wherein:
   X is absent or present and when X is present X is selected from the group consisting of acetyl, butyryl, hexanoyl, methoxy-PEG$_{(n)}$CO, hydroxy-PEG$_{(n)}$CO, amino-PEG$_{(n)}$CO, and sarcosyl-amino-PEG$_{(n)}$CO where n is 3-13, and X is in an amide bond to an amino terminus of AA0, AA1, or AA2;
   B is absent or present and when B is present B is a di-carboxylic acid containing from 4-8 carbon atoms, which may be straight-chain or branched, and B is in a half-amide bond to an amino terminus of X, or B is in a half-amide bond to an amino terminus of AA0 when X is absent or B is in a half-amide bond to an amino terminus of AA1 when X and AA0 are absent or B is in a half-amide bond to an amino terminus of AA2 when X, AA0 and AA1 are absent; and B may end in a free carboxyl group, or this otherwise free carboxyl group may be in an ester bond to a hydroxyl group of Z; and
   Z is absent or present if B is present, Z is absent if X is present, and when Z is present Z is joined through an ester bond to a carbonyl group of B and Z is selected from the group consisting of: primary or secondary hydroxyl groups of sugar monomers present on a polymeric carbohydrate carrier; hydroxyl groups of a hydroxyl terminal dendrimer; and primary or secondary hydroxyl groups of acyclic or cyclic amino alcohols having between 4 and 6 carbon atoms and a single primary or secondary amine that is protected through an amide bond or a carbamate bond;
   wherein if B is present X is absent and wherein if X is present B is absent.

2. The modified peptide of claim 1, wherein B is present and is adipic acid or glutaric acid in half amide bond to AA0, or B is in a half-amide bond to an amino terminus of AA1 when AA0 is absent or B is in a half-amide bond to an amino terminus of AA2 when AA0 and AA1 are absent.

3. The modified peptide of claim 1, wherein B is present and selected from the group consisting of succinic acid, glutaric acid, adipic acid, and suberic acid.

4. The modified peptide of claim 3, wherein AA1 through AA8 are: Sar/Gly-Tyr-Asn-Leu-Tyr-Arg-Val-Pro (SEQ ID NO: 15).

5. The modified peptide of claim 2 wherein AA2 through AA6 are: Tyr-Asn-Leu-Tyr-Arg (SEQ ID NO: 14).

6. A prodrug comprising:
   (a) a carrier particle comprising carboxyl groups or hydroxyl groups; and
   (b) the modified peptide of claim 1 conjugated to the polymeric carrier particle.

7. The prodrug of claim 6, wherein the prodrug further comprises an amino alcohol linker that links the peptide to the carrier particle, the peptide is esterified to a free hydroxyl group of the linker, the linker is attached to the carrier particle via the amino group of the linker and a free hydroxyl group of the carrier particle forming a carbamate bond, or via the amino group of the linker and a free carboxyl group of the carrier particle forming an amide bond.

8. The prodrug of claim 6, wherein the linker is selected from the group consisting of amino-n-butoxy, amino-ethoxyethyloxy, amino-piperidyl(3, or 4)-oxy, amino-pyrrolidinyl(3)-oxy, amino-benzyloxy, BOC-aminoethylamido-valeric acid (4)-oxy, amino-cyclohexyl (3, or 4)-oxy, and amino-cyclopentyl (3)-oxy.

9. The prodrug of claim 6, wherein the carrier particle comprises dextrin, dextran, or hyaluronic acid.

10. A pharmaceutical composition comprising the modified peptide of claim 1 or a prodrug thereof and a pharmaceutical carrier.

11. A method of treating and/or preventing cancer in a subject in need thereof, the method comprising administering the pharmaceutical composition of claim 10 to the subject.

12. A method of treating and/or preventing infectious disease in a subject having immune system exhaustion characterized by elevated PD-L1, the method comprising administering the pharmaceutical composition of 10 claim to the subject.

13. A method of treating and/or preventing an eye disease or disorder in a subject in need thereof, the method comprising administering the pharmaceutical composition of claim 10 to the subject.

14. A method of treating and/or preventing a kidney disease or disorder in a subject in need thereof, the method comprising administering the pharmaceutical composition of claim 10 to the subject.

15. A method of treating and/or preventing an ear disease or disorder in a subject in need thereof, the method comprising administering the pharmaceutical composition of claim 10 to the subject.

16. A modified peptide comprising:
(a) a peptide consisting of an amino acid of AA0-AA1-AA2-AA3-AA4-AA5-AA6-AA7-AA8-AA9-AA10 (SEQ ID NO:14), wherein:
AA0 is absent or present and when AA0 is present AA0 is selected from the group consisting of sarcosyl and Gly;
AA1 is absent or present and when AA1 is present AA1 is selected from the group consisting of sarcosyl and Gly;
AA2 is Tyr;
AA3 Asn;
AA4 is Leu, Ile, or Val;
AA5 is Tyr or Phe;
AA6 is Arg;
AA7 is Val or Pro;
AA8 is present or absent and when AA8 is present AA8 is selected from the group consisting of Arg, Pro, and Gln;
AA9 is present or absent and when AA9 is present AA9 is selected from the group consisting of Ser and Ala; and
AA10 is absent or present and when AA10 is present AA10 is selected from the group consisting of Ser and Ser-Thr; and
(b) one or more non-amino acid moieties, wherein one of said one or more non-amino acid moieties comprises -Y linked to the C-terminal end of the peptide, wherein Y is an amide or a substituted amide selected from the group consisting of amide or ethylamide.

17. The modified peptide of claim 16, wherein AA2 through AA6 are: Tyr-Asn-Leu-Tyr-Arg (SEQ ID NO: 14).

18. A prodrug comprising:
(a) a carrier particle comprising carboxyl groups or hydroxyl groups; and
(b) the modified peptide of claim 17 conjugated to the polymeric carrier particle.

19. A pharmaceutical composition comprising the modified peptide of claim 17 or a prodrug thereof and a pharmaceutical carrier.

20. A method comprising administering the pharmaceutical composition of claim 19 to a subject.

21. A prodrug comprising:
(a) a dextrin, dextran, or hyaluronic acid carrier particle; and
(b) a modified peptide conjugated to the polymeric carrier particle via a linker, wherein the modified peptide comprises:
(i) a peptide consisting of an amino acid of AA0-AA1-AA2-AA3-AA4-AA5-AA6-AA7-AA8-AA9-AA10 (SEQ ID NO:14), wherein:
AA0 is absent or present and when AA0 is present AA0 is selected from the group consisting of sarcosyl and Gly;
AA1 is absent or present and when AA1 is present AA1 is selected from the group consisting of sarcosyl and Gly;
AA2 is Tyr;
AA3 is Asn;
AA4 is Leu, Ile, or Val;
AA5 is Tyr or Phe;
AA6 is Arg;
AA7 is Val or Pro;
AA8 is present or absent and when AA8 is present AA8 is selected from the group consisting of Arg, Pro, and Gln;
AA9 is present or absent and when AA9 is present AA9 is selected from the group consisting of Ser and Ala; and
AA10 is absent or present and when AA10 is present AA10 is selected from the group consisting of Ser and Ser-Thr; and
(ii) one or more non-amino acid moieties on the N-terminal and/or C-terminal end of the peptide.

22. The prodrug of claim 21, wherein the prodrug further comprises an amino alcohol linker that links the peptide to the carrier particle, the peptide is esterified to a free hydroxyl group of the linker, the linker is attached to the carrier particle via the amino group of the linker and a free hydroxyl group of the carrier particle forming a carbamate bond, or via the amino group of the linker and a free carboxyl group of the carrier particle forming an amide bond.

23. The prodrug of claim 21, wherein the linker is selected from the group consisting of amino-n-butoxy, amino-ethoxyethyloxy, amino-piperidyl(3, or 4)-oxy, amino-pyrrolidinyl(3)-oxy, amino-benzyloxy, BOC-aminoethylamido-valeric acid (4)-oxy, amino-cyclohexyl (3, or 4)-oxy, and amino-cyclopentyl (3)-oxy.

24. A pharmaceutical composition comprising the prodrug of claim 21 and a pharmaceutical carrier.

25. A method comprising administering the pharmaceutical composition of claim 24 to a subject.

* * * * *